(12) United States Patent
Kale et al.

(10) Patent No.: US 10,993,647 B2
(45) Date of Patent: May 4, 2021

(54) DROWSINESS DETECTION FOR VEHICLE CONTROL

(71) Applicant: Micron Technology, Inc., Boise, ID (US)

(72) Inventors: Poorna Kale, Folsom, CA (US); Robert Richard Noel Bielby, Placerville, CA (US)

(73) Assignee: Micron Technology, Inc., Boise, ID (US)

( * ) Notice: Subject to any disclaimer, the term of this patent is extended or adjusted under 35 U.S.C. 154(b) by 0 days.

(21) Appl. No.: 16/547,136

(22) Filed: Aug. 21, 2019

(65) Prior Publication Data
US 2021/0052206 A1  Feb. 25, 2021

(51) Int. Cl.
| G08B 23/00 | (2006.01) |
| A61B 5/18 | (2006.01) |
| G08B 21/06 | (2006.01) |
| G06N 20/00 | (2019.01) |
| G06K 9/00 | (2006.01) |
| B60K 28/06 | (2006.01) |
| G06N 3/02 | (2006.01) |

(52) U.S. Cl.
CPC ............ *A61B 5/18* (2013.01); *G06K 9/00845* (2013.01); *G06N 20/00* (2019.01); *G08B 21/06* (2013.01); *B60K 28/06* (2013.01); *G06N 3/02* (2013.01)

(58) Field of Classification Search
None
See application file for complete search history.

(56) References Cited

U.S. PATENT DOCUMENTS

| 5,745,031 | A | * | 4/1998 | Yamamoto | B60K 28/066 340/439 |
| 6,097,295 | A | * | 8/2000 | Griesinger | A61B 5/18 340/576 |
| 6,661,345 | B1 | * | 12/2003 | Bevan | G08B 21/06 340/575 |
| 9,802,571 | B2 | | 10/2017 | Shreve et al. | |
| 10,013,773 | B1 | | 7/2018 | Ogale et al. | |
| 10,507,793 | B1 | | 12/2019 | De Moura | |
| 2001/0002936 | A1 | | 6/2001 | Tsuji et al. | |
| 2004/0036261 | A1 | | 2/2004 | Breed | |
| 2004/0090314 | A1 | | 5/2004 | Iwamoto | |
| 2004/0193347 | A1 | | 9/2004 | Harumoto et al. | |

(Continued)

OTHER PUBLICATIONS

Title: Automotive Predictive Maintenance, U.S. Appl. No. 16/538,006, filed Aug. 12, 2019, Inventors: Robert Bielby et al., Status: Docketed New Case—Ready for Examination, Status Date: Sep. 25, 2019.

(Continued)

*Primary Examiner* — Julie B Lieu
(74) *Attorney, Agent, or Firm* — Greenberg Traurig

(57) ABSTRACT

Systems, methods and apparatus of drowsiness detection for vehicle control. For example, a vehicle includes: a camera configured to face a driver of the vehicle and generate a sequence of images of the driver driving the vehicle; an artificial neural network configured to analyze the sequence of images and classify, based on the sequence of images, whether the driver is in a drowsy state; and an infotainment system configured to provide instructions to the driver in response to a classification by the artificial neural network that the driver is in the drowsy state.

17 Claims, 15 Drawing Sheets

(56) References Cited

U.S. PATENT DOCUMENTS

| | | | |
|---|---|---|---|
| 2005/0201565 A1 | 9/2005 | Choi et al. | |
| 2005/0270178 A1 | 12/2005 | Ioli | |
| 2005/0285758 A1 | 12/2005 | Matsukawa et al. | |
| 2007/0008151 A1* | 1/2007 | Victor | A61B 5/1122 340/573.1 |
| 2007/0065002 A1 | 3/2007 | Marzell et al. | |
| 2007/0279493 A1 | 12/2007 | Edanami | |
| 2008/0007567 A1 | 1/2008 | Clatworthy et al. | |
| 2008/0036187 A1 | 2/2008 | Breed | |
| 2008/0260239 A1 | 10/2008 | Han et al. | |
| 2010/0109881 A1* | 5/2010 | Eskandarian | B60K 28/066 340/575 |
| 2010/0191391 A1 | 7/2010 | Zeng | |
| 2014/0036076 A1 | 2/2014 | Nerayoff et al. | |
| 2014/0132423 A1 | 5/2014 | Choi et al. | |
| 2014/0222288 A1 | 8/2014 | Lavoie et al. | |
| 2014/0236472 A1 | 8/2014 | Rosario | |
| 2015/0195518 A1 | 7/2015 | Shikii et al. | |
| 2015/0206014 A1 | 7/2015 | Wu et al. | |
| 2015/0217449 A1 | 8/2015 | Meier et al. | |
| 2016/0203377 A1 | 7/2016 | Irie et al. | |
| 2017/0177965 A1 | 6/2017 | Gordo Soldevila et al. | |
| 2017/0300788 A1 | 10/2017 | Cao et al. | |
| 2017/0327094 A1 | 11/2017 | Inoue et al. | |
| 2017/0371340 A1 | 12/2017 | Cohen et al. | |
| 2018/0173961 A1* | 6/2018 | Jain | G06T 7/40 |
| 2018/0173971 A1 | 6/2018 | Jia et al. | |
| 2018/0181822 A1 | 6/2018 | Chang et al. | |
| 2019/0065867 A1 | 2/2019 | Huang et al. | |
| 2019/0077409 A1* | 3/2019 | Zandi | B60W 40/08 |
| 2019/0147051 A1 | 5/2019 | Lu et al. | |
| 2019/0184916 A1 | 6/2019 | Troia et al. | |
| 2019/0187291 A1 | 6/2019 | Troia | |
| 2019/0197795 A1 | 6/2019 | Mondello et al. | |
| 2019/0205744 A1 | 7/2019 | Mondello et al. | |
| 2019/0286414 A1 | 9/2019 | Langos | |
| 2019/0367049 A1* | 12/2019 | Oba | B60W 50/08 |
| 2020/0007672 A1 | 1/2020 | Reyes et al. | |
| 2020/0062275 A1* | 2/2020 | Higgins | G06K 9/00845 |
| 2020/0070657 A1* | 3/2020 | Kim | A61B 5/05 |
| 2020/0202151 A1* | 6/2020 | Wacquant | G06K 9/00845 |
| 2020/0231182 A1* | 7/2020 | Oba | B60W 40/09 |

OTHER PUBLICATIONS

Title: Storage Devices With Neural Network Accelerators for Automotive Predictive Maintenance, U.S. Appl. No. 16/538,011, filed Aug. 12, 2019, Inventors: Poorna Kale et al., Status: Docketed New Case—Ready for Examination, Status Date: Sep. 5, 2019.

Title: Storage and Access of Neural Network Models of Automotive Predictive Maintenance, U.S. Appl. No. 16/538,015, filed Aug. 12, 2019, Inventors: Robert Bielby et al., Status: Docketed New Case—Ready for Examination, Status Date: Feb. 19, 2020.

Title: Storage and Access of Neural Network Inputs in Automotive Predictive Maintenance, U.S. Appl. No. 16/538,073, filed Aug. 12, 2019, Inventors: Poorna Kale et al., Status: Docketed New Case—Ready for Examination, Status Date: Sep. 5, 2019.

Title: Storage and Access of Neural Network Outputs in Automotive Predictive Maintenance, U.S. Appl. No. 16/538,078, filed Aug. 12, 2019, Inventors: Robert Bielby et al., Status: Docketed New Case—Ready for Examination, Status Date: Feb. 19, 2020.

Title: Communications Between Processors and Storage Devices in Automotive Predictive Maintenance Implemented via Artificial Neural Networks, U.S. Appl. No. 16/538,087, filed Aug. 12, 2019, Inventors: Poorna Kale et al., Status: Docketed New Case—Ready for Examination, Status Date: Sep. 3, 2019.

Title: Predictive Maintenance of Automotive Engines, U.S. Appl. No. 16/538,092, filed Aug. 12, 2019, Inventors: Robert Bielby et al., Status: Docketed New Case—Ready for Examination, Status Date: Feb. 19, 2020.

Title: Predictive Maintenance of Automotive Battery, U.S. Appl. No. 16/538,097, filed Aug. 12, 2019, Inventors: Poorna Kale et al., Status: Docketed New Case—Ready for Examination, Status Date: Feb. 19, 2020.

Title: Predictive Maintenance of Automotive Powertrain, U.S. Appl. No. 16/538,103, filed Aug. 12, 2019, Inventors: Robert Bielby et al., Status: Docketed New Case—Ready for Examination, Status Date: Sep. 25, 2019.

Title: Predictive Maintenance of Automotive Lighting, U.S. Appl. No. 16/538,108, filed Aug. 12, 2019, Inventors: Poorna Kale et al., Status: Docketed New Case—Ready for Examination, Status Date: Sep. 25, 2019.

Title: Predictive Maintenance of Automotive Tires, U.S. Appl. No. 16/538,121, filed Aug. 12, 2019, Inventors: Robert Bielby et al., Status: Docketed New Case—Ready for Examination, Status Date: Sep. 5, 2019.

Title: Monitoring Controller Area Network Bus for Vehicle Control, U.S. Appl. No. 16/547,149, filed Aug. 21, 2019, Inventors: Robert Bielby et al., Status: Application Dispatched from Preexam, Not Yet Docketed, Status Date: Sep. 30, 2019.

Title: Intelligent Climate Control in Vehicles, U.S. Appl. No. 16/547,165, filed Aug. 21, 2019, Poorna Kale et al., Status: Docketed New Case—Ready for Examination, Status Date: Sep. 25, 2019.

Title: Intelligent Audio Control in Vehicles, U.S. Appl. No. 16/547,177, filed Robert Bielby et al., Status: Docketed New Case—Ready for Examination, Status Date: Oct. 4, 2019.

Title: Security Operations of Parked Vehicles, U.S. Appl. No. 16/547,185, filed Aug. 21, 2019, Inventors: Poorna Kale et al., Status: Docketed New Case—Ready For Examination, Status Date: Jan. 7, 2020.

Title: Intelligent Recording of Errant Vehicle Behaviors, U.S. Appl. No. 16/547,199, filed Aug. 21, 2019, Inventors: Robert Bielby et al., Status: Application Dispatched from Preexam, Not Yet Docketed, Status Date: Sep. 30, 2019.

Title: Predictive Maintenance of Automotive Transmission, U.S. Appl. No. 16/719,181, filed Dec. 18, 2019, Inventors: Poorna Kale et al., Status: Application Dispatched from Preexam, Not Yet Docketed, Status Date: Feb. 24, 2020.

Title: Monitoring of Drive by Wire Sensors in Vehicles, U.S. Appl. No. 16/791,870, Filed on:, Inventors: Robert Bielby et al., Status: Application Undergoing Preexam Processing, Status Date: Feb. 14, 2020.

Title: Optimization of Power Usage of Data Storage Devices, U.S. Appl. No. 16/791,887, Filed on:, Inventors: Poorna Kale et al., Status: Application Undergoing Preexam Processing, Status Date: Feb. 14, 2020.

Title: Temperature based Optimization of Data Storage Operations, U.S. Appl. No. 16/562,197, filed Sep. 5, 2019, Inventors: Robert Bielby et al., Status: Docketed New Case—Ready for Examination, Status Date: Oct. 25, 2019.

Title: Predictive Management of Failing Portions in a Data Storage Device, U.S. Appl. No. 16/562,211, filed Sep. 5, 2019, Inventors: Poorna Kale et al., Status: Docketed New Case—Ready for Examination, Status Date: Sep. 25, 2019.

Title: Intelligent Optimization of Caching Operations in a Data Storage Device, U.S. Appl. No. 16/562,213, filed Sep. 5, 2019, Inventors: Robert Bielby et al., Status: Docketed New Case—Ready for Examination, Status Date: Sep. 23, 2019.

Title: Intelligent Write-Amplification Reduction for Data Storage Devices Configured on Autonomous Vehicles, U.S. Appl. No. 16/562,222, filed Sep. 5, 2019, Inventors: Poorna Kale et al., Status: Docketed New Case—Ready for Examination, Status Date: Feb. 19, 2020.

Title: Intelligent Wear Leveling with Reduced Write-Amplification for Data Storage Devices Configured on Autonomous Vehicles, U.S. Appl. No. 16/562,225, filed Sep. 5, 2019, Inventors: Robert Bielby et al., Status: Docketed New Case—Ready for Examination, Status Date: Sep. 23, 2019.

Title: Bandwidth Optimization for Different Types of Operations Scheduled in Data Storage Device, U.S. Appl. No. 16/562,230, filed

(56) References Cited

OTHER PUBLICATIONS

Sep. 5, 2019, Inventors: Poorna Kale et al., Status: Docketed New Case—Ready for Examination, Status Date: Oct. 15, 2019.

* cited by examiner

DROWSINESS DETECTION FOR VEHICLE CONTROL

FIELD OF THE TECHNOLOGY

At least some embodiments disclosed herein relate to vehicles in general and more particularly, but not limited to, detection of drowsiness in vehicle drivers.

BACKGROUND

Recent developments in the technological area of autonomous driving allow a computing system to operate, at least under some conditions, control elements of a motor vehicle without the assistance from a human operator of the vehicle.

For example, sensors (e.g., cameras and radars) can be installed on a motor vehicle to detect the conditions of the surroundings of the vehicle traveling on a roadway. A computing system installed on the vehicle analyzes the sensor inputs to identify the conditions and generate control signals or commands for the autonomous adjustments of the direction and/or speed of the vehicle, with or without any input from a human operator of the vehicle.

In some arrangements, when a computing system recognizes a situation where the computing system may not be able to continue operating the vehicle in a safe manner, the computing system alerts the human operator of the vehicle and requests the human operator to take over the control of the vehicle and drive manually, instead of allowing the computing system to drive the vehicle autonomously.

Autonomous driving and/or advanced driver assistance system (ADAS) typically involves artificial neural network (ANN) for the identification of events and/or objects that are captured in sensor inputs.

In general, an artificial neural network (ANN) uses a network of neurons to process inputs to the network and to generate outputs from the network.

For example, each neuron in the network receives a set of inputs. Some of the inputs to a neuron may be the outputs of certain neurons in the network; and some of the inputs to a neuron may be the inputs provided to the neural network. The input/output relations among the neurons in the network represent the neuron connectivity in the network.

For example, each neuron can have a bias, an activation function, and a set of synaptic weights for its inputs respectively. The activation function may be in the form of a step function, a linear function, a log-sigmoid function, etc. Different neurons in the network may have different activation functions.

For example, each neuron can generate a weighted sum of its inputs and its bias and then produce an output that is the function of the weighted sum, computed using the activation function of the neuron.

The relations between the input(s) and the output(s) of an ANN in general are defined by an ANN model that includes the data representing the connectivity of the neurons in the network, as well as the bias, activation function, and synaptic weights of each neuron. Using a given ANN model a computing device computes the output(s) of the network from a given set of inputs to the network.

For example, the inputs to an ANN network may be generated based on camera inputs; and the outputs from the ANN network may be the identification of an item, such as an event or an object.

A spiking neural network (SNN) is a type of ANN that closely mimics natural neural networks. An SNN neuron produces a spike as output when the activation level of the neuron is sufficiently high. The activation level of an SNN neuron mimics the membrane potential of a natural neuron. The outputs/spikes of the SNN neurons can change the activation levels of other neurons that receive the outputs. The current activation level of an SNN neuron as a function of time is typically modeled using a differential equation and considered the state of the SNN neuron. Incoming spikes from other neurons can push the activation level of the neuron higher to reach a threshold for spiking. Once the neuron spikes, its activation level is reset. Before the spiking, the activation level of the SNN neuron can decay over time, as controlled by the differential equation. The element of time in the behavior of SNN neurons makes an SNN suitable for processing spatiotemporal data. The connectivity of SNN is often sparse, which is advantageous in reducing computational workload.

In general, an ANN may be trained using a supervised method where the parameters in the ANN are adjusted to minimize or reduce the error between known outputs resulted from respective inputs and computed outputs generated from applying the inputs to the ANN. Examples of supervised learning/training methods include reinforcement learning, and learning with error correction.

Alternatively, or in combination, an ANN may be trained using an unsupervised method where the exact outputs resulted from a given set of inputs is not known before the completion of the training. The ANN can be trained to classify an item into a plurality of categories, or data points into clusters.

Multiple training algorithms can be employed for a sophisticated machine learning/training paradigm.

U.S. Pat. No. 9,533,579, entitled "Electronic Control Apparatus for Electrically-Driven Vehicle" and published Jan. 3, 2017, discloses an electronic control apparatus of a vehicle that has a self-diagnosis function.

Automotive maintenance is conventionally scheduled based on a predetermined milestone of operations. For example, a routine maintenance service can be scheduled once for every three or six months, or after a predetermined distance traveled (e.g., 3000 miles, 6000 miles, or 15000 miles).

When a component of a motor vehicle breaks down or malfunctions during the operation of the vehicle, such an incident can be a safety hazard. After such an incident occurs, a trip for the service of the vehicle would be scheduled soon at an inconvenient time.

BRIEF DESCRIPTION OF THE DRAWINGS

The embodiments are illustrated by way of example and not limitation in the figures of the accompanying drawings in which like references indicate similar elements.

DETAILED DESCRIPTION

At least some embodiments disclosed herein provide systems, methods and apparatus to process sensor data generated in a motor vehicle, or another vehicle with or without an advanced driver assistance system (ADAS).

Before a component of a motor vehicle breaks down or malfunctions during the operation of a vehicle, there can be indication of whether the component needs replacement or maintenance. Such indications may not be noticeable to a typical driver or passengers. However, sensor data can be collected and analyzed to predict the probability of component failures. The prediction can be used to schedule maintenance services, which can reduce or eliminate the chances of incidents where a component of a vehicle breaks down or malfunctions during the operation of the vehicle on a roadway. Further, the prediction allows the service trip to be scheduled at a convenient time.

For example, sensors can be installed in an automotive system to collect data during its routine operations; and the sensor data can be used to predict whether and how soon a component needs replacement or maintenance. The sensor data can be provided as input to an artificial neural network (ANN) (e.g., spiking neural network (SNN)) of an artificial intelligent (AI) system to train itself (e.g., using an unsupervised machine learn technique) in a time period in which the vehicle is expected to operate normally. The training customizes the neural network for the specific operating environment(s) of the driver, passenger, or user of the vehicle and the personalized operating habits of the vehicle occupant(s). Subsequently, when the operating data deviates the normal mode, the artificial neural network can detect abnormal conditions. The AI system can be used to suggest a maintenance service and/or identify the component that likely needs replacement or maintenance.

Figure 1:
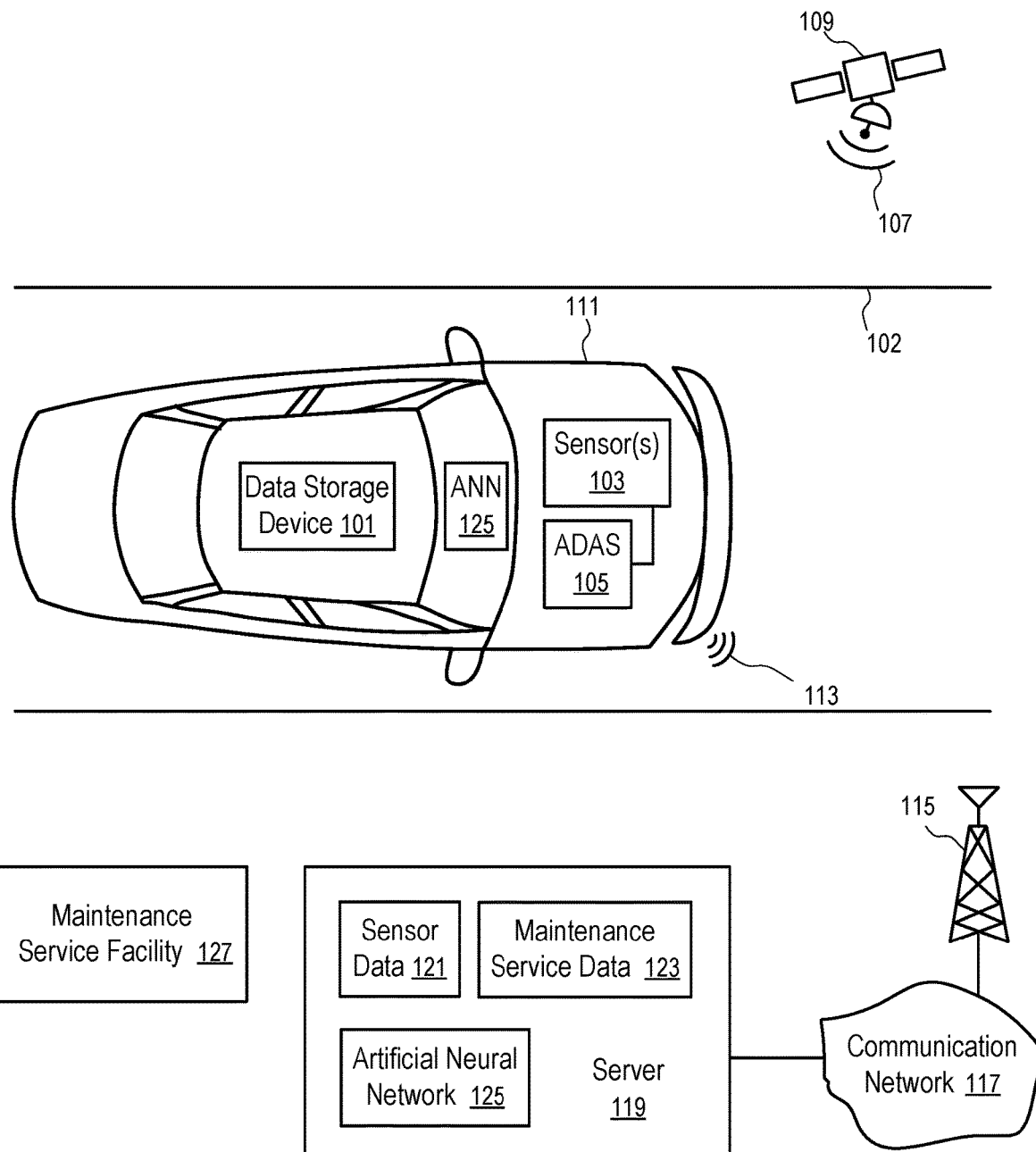
FIG. 1 shows a system in which a vehicle is configured with a data storage device to collect and process sensor data according to some embodiments.

FIG. 1 shows a system in which a vehicle is configured with a data storage device to collect and process sensor data according to some embodiments.

The system of FIG. 1 includes a vehicle (111) having a data storage device (101). Optionally, the vehicle (111) has an advanced driver assistance system (ADAS) (105) and one or more sensors (103) that provide senor data input to the ADAS (105) and/or the data storage device (101). The data storage device (101) is configured to use an artificial neural network (ANN) (125) to predict/identify a need for a maintenance service based on the data collected by the sensors (103). The ADAS (105) can be omitted without impacting the predictive maintenance features. In some implementations, at least a portion of the data generate by the sensors (103) is used in both the ADAS (105) for driver assistance and in the ANN (125) for maintenance prediction. Optionally, the output of the ANN (124) can be used in both the data storage device (101) and in the ADAS (105).

The sensor(s) (103) can include digital cameras, lidars, radars, ultrasound sonars, brake sensors, speed sensors, acceleration sensors, airbag sensors, a GPS (global positioning system) receiver, audio sensors/microphones, vibration sensors, force/stress sensors, deformation sensors, motion sensors, temperature sensors, etc. Some of the sensors (103) can be configured primarily to monitor the environment of the vehicle (111); and other sensors (103) can be configured primarily to monitor the operating condition of one or more component of the vehicle (111), such as an internal combustion engine, an exhaust system, an electric motor, a brake, a tire, a battery, etc.

The outputs of the sensor(s) (103) as a function of time are provided as a sensor data stream to the ADAS (105) and/or the ANN (125) to provide driver assistance (e.g., autonomous driving) and maintenance prediction.

For example, the vehicle (111) can have a wireless communication device to communicate with a remote server (119) via wireless signals (113) and a communication network (117). The remote server (119) is typically configured at a location away from a road (102) on which the vehicle (111) is in service. For example, the vehicle (111) may provide some sensor data (121) to the server (119) and receive update of the ANN (125) from the server (119).

One example of the communication network (117) is a cell phone network having one or more base stations (e.g., 115) to receive the wireless signals (e.g., 113). Another example of the communication network (117) is internet, where the wireless local area network signals (e.g., 113) transmitted by the vehicle (113) is received in an access point (e.g., 115) for further communication to the server (119). In some implementations, the vehicle (111) uses a communication link (107) to a satellite (109) or a communication balloon to communicate with the server (119).

The server (119) can also communicate with one or more maintenance service facilities (e.g., 127) to receive maintenance service data (123) of vehicles (e.g., 111). The maintenance service data (123) can include inspection records and/or service records of components of the vehicles (e.g., 111). For example, the inspection records and/or service records can indicate the degree of wear and tear of components inspected during their services at the maintenance service facilities (e.g., 127), the identification of failed or malfunctioning components, etc. The sensor data (121) of the vehicles (e.g., 111) in a time period prior to the services and the maintenance service data (123) can be used to train an ANN (125) to predict the probability of a component requiring a maintenance service. The updated ANN (125) can be used to predict and suggest a maintenance service for a vehicle (111) based on sensor data (121) received in a recent period of time. Alternatively, the update ANN (125) can be transmitted to the vehicle (111); and the vehicle (111) can used the data generated from the sensors (103) during routine operations of the vehicle (111) to predict and suggest a maintenance service.

The data storage device (101) of the vehicle (111) can be configured to record sensor data for a period of time that can be used in the ANN for predictive maintenance. Maintenance prediction is typically for a relative long period of time (e.g., a few days, weeks and/or months). In contrast, sensor data recorded for the review of an accident, collision, or near collision involving an autonomous vehicle is typically for a short period of time (e.g., 30 seconds to a few minutes). Thus, a typical black box data recorder configured to record sensor data for the review/analysis of an accident or collision is insufficient for predictive maintenance.

Optionally, the data storage device (101) stores the sensor data of a period of time leading to a trip to a maintenance service facility (e.g., 127). The maintenance service facility (e.g., 127) can download the sensor data (121) from the data storage device (101) and provide the sensor data (121) and the corresponding maintenance service data (123) to the server (119) to facilitate the training of the ANN (125).

Optionally, or in combination, the data storage device (101) is configured with a machine learning module to customize and/or train the ANN (125) installed in the vehicle (111) for predictive maintenance.

For example, the machine learning module of the data storage device (101) can be used to calibrate the ANN (125) to account for the typical/daily environment in which the vehicle (111) is being operated and/or driving preferences/habits of the driver(s) of the vehicle (111).

For example, during a period of time when the vehicle is expected to be operated under typical/daily environment with healthy components, the sensor data generated by the sensors (103) can be used to train the ANN (125) to recognize the patterns of sensor data that represents trouble free operations. Such patterns can vary for different vehicles (e.g., 111) based on their routine operating environments and the driving habits/characteristics of their drivers. The training allows the ANN (125) to detect deviations from the recognized normal patterns and report anomaly for maintenance predictions.

For example, the ANN (125) can include an SNN configured to classify time-based variations of sensor data and/or detect deviation from known patterns of sensor data of the vehicle (111) operated in the normal/healthy condition but in a personalized environment (e.g., a daily route of a driver/passenger) and/or operated under a personalized driving habit/pattern.

Figure 2:
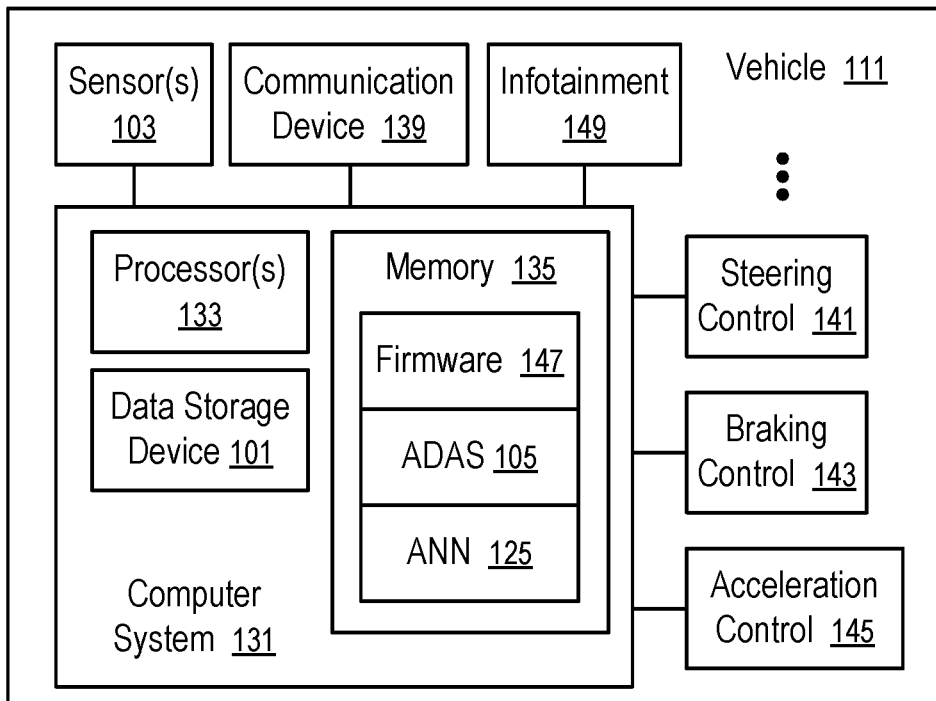
FIG. 2 shows an autonomous vehicle having a data storage device according to one embodiment.

FIG. 2 shows an autonomous vehicle (111) having a data storage device (101) according to one embodiment. For example, the vehicle (111) in the system of FIG. 1 can be implemented using the autonomous vehicle (111) of FIG. 2.

The vehicle (111) of FIG. 2 is configured to have an advanced driver assistance system (ADAS) (105). The ADAS (105) of the vehicle (111) can have an Artificial Neural Network (ANN) (125) for object detection, recognition, identification, and/or classification. The ANN (125) and/or another neural network (e.g., configured in the data storage device (101)) can be used to predict the probability of a component of the vehicle (111) requiring a maintenance service (e.g., repair, replacement, or adjustment).

Preferably, the data storage device (101) is configured to process sensor data at least partially for predictive maintenance with reduced computation burden on the processors (133) that are tasked to operate the ADAS (105) and/or other components, such as an infotainment system (149).

The vehicle (111) typically includes an infotainment system (149), a communication device (139), one or more sensors (103), and a computer system (131) that is connected to some controls of the vehicle (111), such as a steering control (141) for the direction of the vehicle (111), a braking control (143) for stopping of the vehicle (111), an acceleration control (145) for the speed of the vehicle (111), etc. In some embodiments, the vehicle (111) in the system of FIG. 1 has a similar configuration and/or similar components.

Some of the sensors (103) are required for the operations of the ADAS (105); and some of the sensors (103) are used to collect data related to the health of the components of the vehicle (111), which may not be used in the ADAS (105). Optionally, the sensor data generated by the sensors (103) can also be used to predict the likelihood of imminent failure of a component. Such a prediction can be used in the ADAS (105) to take emergency actions to render the vehicle in a safe state (e.g., by reducing speed and/or pulling off to park).

The computer system (131) of the vehicle (111) includes one or more processors (133), a data storage device (101), and memory (135) storing firmware (or software) (147), including the computer instructions and data models for ADAS (105).

The one or more sensors (103) of the vehicle can include a visible light camera, an infrared camera, a lidar, radar, or sonar system, a peripheral sensor, a global positioning system (GPS) receiver, a satellite positioning system receiver, a brake sensor, and/or an airbag sensor. Further, the sensors (103) can include audio sensors (e.g., microphone) configured to monitor noises from various components and locations in the vehicle (111), a vibration sensor, a pressure sensor, a force sensor, a stress sensor, and/or a deformation sensor configured to measure loads on a component of the vehicle (111), accelerometers and/or gyroscope sensors measuring the motions of some components of the vehicle (111), etc. Such sensors can be used to monitor the operating status and/or health of the components for predictive maintenance.

The sensor(s) (103) can provide a stream of real time sensor data to the computer system (131). The sensor data generated by a sensor (103) of the vehicle (111) can include an image that captures an object using a camera that images using lights visible to human eyes, or a camera that images using infrared lights, or a sonar, radar, or LIDAR system. Image data obtained from at least one sensor of the vehicle is part of the collected sensor data for recording in the data storage device (101) and/or as input to the ANN (125). For example, a camera can be used to obtain roadway information for the travel of the vehicle (111), which can be processed by the ANN (125) to generate control signals for the vehicle (111). For example, a camera can be used to monitor the operation state/health of a component of the vehicle (111), which can be processed by the ANN (125) to predict or schedule a maintenance service.

The sensor data generated by a sensor (103) of the vehicle (111) can include an audio stream that captures the characteristics of sounds at a location on the vehicle (111), such as a location near an engine, a motor, a transmission system, a wheel, a door, a window, etc. The audio data obtained from at least one sensor (103) of the vehicle (111) can be part of the collected sensor data for recording in the data storage device (101) and/or as input to the ANN (125). For example, the audio stream can be used to monitor the operation state/health of a component of the vehicle (111) (e.g., an internal combustion engine, an exhaust system, an electric motor, a brake), which can be processed by the ANN (125) to predict or schedule a maintenance service.

The infotainment system (149) can be used to present the predicted or schedule maintenance service. Optionally, the communication device (139) can establish a connection to a mobile device of the driver of the vehicle (111) to inform the driver of the recommended maintenance service and/or the recommended data of the service, to calendar the appointment, etc.

When the vehicle (111) is configured with an ADAS (105), the outputs of the ADAS (105) can be used to control (e.g., (141), (143), (145)) the acceleration of the vehicle (111), the speed of the vehicle (111), and/or the direction of the vehicle (111), during autonomous driving.

Figure 3:
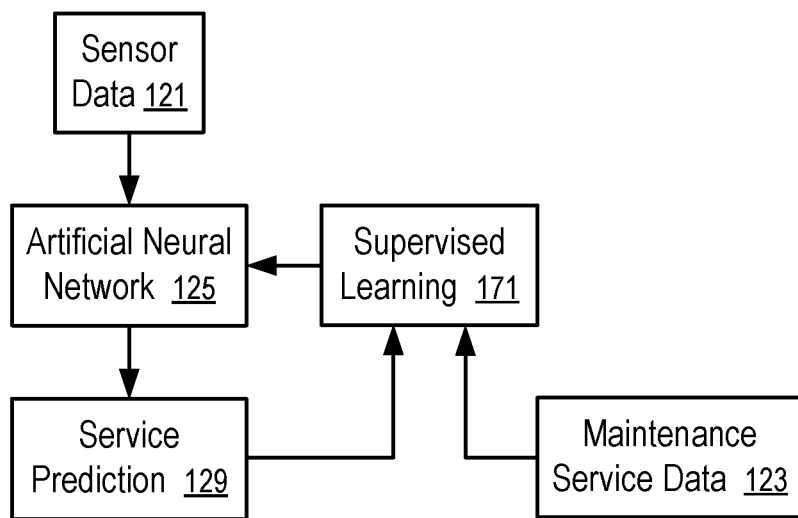
FIGS. 3-5 illustrate training of artificial neural networks for maintenance service prediction according to some embodiments.
Figure 4:
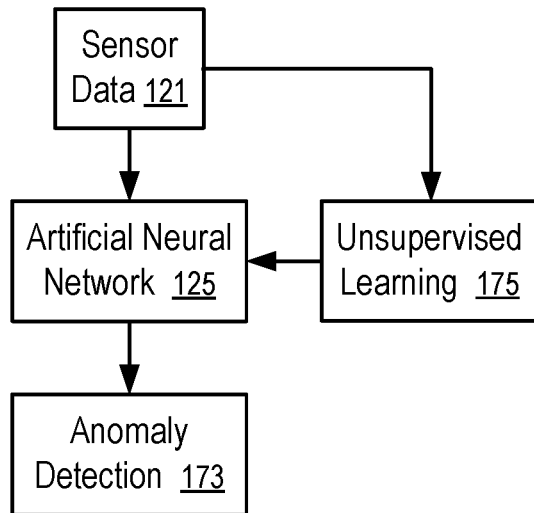
Figure 5:
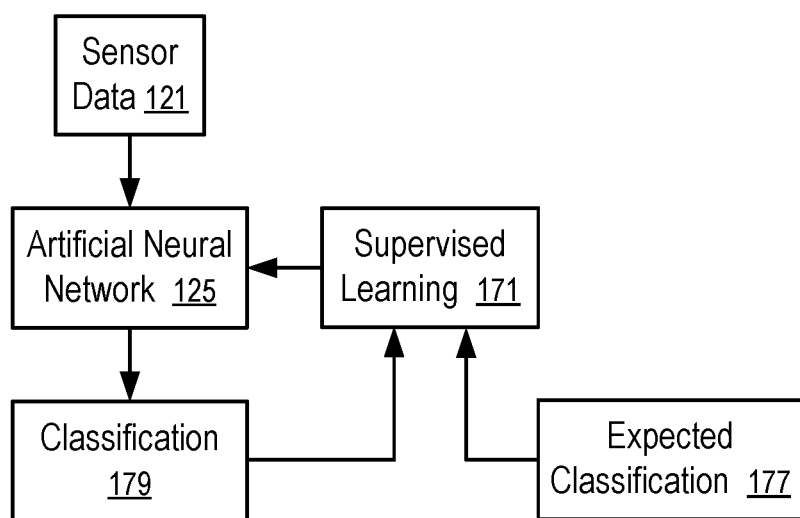

FIGS. 3-5 illustrate training of artificial neural networks for maintenance service prediction according to some embodiments.

In FIG. 3, a module (171) of supervised machine learning is used to train an artificial neural network (125) to minimize the differences between the service prediction (129) generated from the sensor data (121) and the maintenance service data (123).

For example, the maintenance service data (123) can identify the measured wear and tear of a component as a function of time to predict a time to a recommended service. The sensor data (121) can be used in the ANN (125) to generate a predicted time to the recommended service. The supervised machine learning module (171) can adjust the artificial neural network (125) to reduce/minimize the difference between the time predicted based on the sensor data (121) and the time computed from the measurement of wear and tear.

For example, the maintenance service data (123) can identify a component that is replaced or repaired in the maintenance service facility (127). The sensor data (121) recorded for a time period prior to the replacement or repair of the component can be used to calculate the times to the replacement or repair. Further, the segments of the stream of sensor data in the time period before the replacement or repair can be used in the ANN (125) to generate a prediction to the time of the replacement or repair. The supervised learning (171) can be used to adjust the ANN (125) to reduce the predicted time to the replacement or repair and the actual time to the replacement or repair.

The supervised learning (171) of FIG. 2 can be applied in the server (119) based on the sensor data of a population of vehicles and their maintenance service data (123) to generate a generic ANN for the population of the vehicles.

The supervised learning (171) of FIG. 2 can be applied in the vehicle (111) based on the sensor data of the vehicle and its maintenance service data (123) to generate a customized/personalized ANN for the population of the vehicles. For example, a generic ANN can be initially used in the vehicle (111); and the sensor data of the vehicle (111) and its maintenance service data (123) can be used to further train the ANN (125) of the vehicle for customization/personalization of the ANN (125) in the vehicle (111).

In FIG. 4, a module (175) of unsupervised machine learning is used to train or refine an artificial neural network (125) to facilitate anomaly detection (173). The unsupervised machine learning module (175) is configured to adjust the ANN (e.g., SNN) the classification, clustering, or recognized pattern in the sensor data (121) such that a degree of deviation from the classification, clustering, or recognized pattern in the sensor data (121) generated in a recent time period can be used to signal the detection (173) of anomaly. Anomaly detection (173) allows the vehicle (111) to be scheduled for inspection in a maintenance service facility (127). Optionally, after the inspection, maintenance service data (123) can be used to apply a supervised learning (171) to generate more precise predictions to a service, as in FIG. 3.

Typically, a vehicle (111) can be assumed to be operating in a normal/healthy condition in a certain time period. For example, after a new vehicle (111) is initially delivered for service, the vehicle (111) can be assumed to provide trouble-free services for at least a period of time (e.g., a few months). For example, after a time period following the replacement or repair of a component, the component can be assumed to provide trouble-free service for at least a period of time (e.g., a few months or a year). Thus, the sensor data (121) obtained during this period of time can be pre-classified as "normal" to train the ANN (125) using an unsupervised learning (175) as in FIG. 4, or a supervised learning (171) as in FIG. 5.

For example, the sensor data (121) collected via during the "normal" service time period of the vehicle (111) or a component can be classified via an unsupervised learning (175) into a number of clusters. Different clusters may correspond to different types of normal conditions (e.g., traveling on different routes, on roads with different surface conditions, on days with different whether conditions, in different time periods of a day, different days in a week, different mood of driving habits of the driver). When a subsequent sensor data (121) is classified outside of the "normal" clusters, an anomaly is detected.

Optionally, a supervised machine learning (171) can be used to train the ANN (125), as illustrated in FIG. 5. During the "normal" service period of the vehicle (111) or a component, an expected classification (177) can be used to label the sensor data (121). The supervised learning (171) can be used to minimize the classification differences between the predictions (179) made using the ANN (125) according to the sensor data (121) and the expected classification (177). Further, when the sensor data (121) is known to be "abnormal" (e.g., after a diagnosis made in the maintenance service facility (127) or by the user, driver, or passenger of the vehicle (111)), the expected classification (177) can be changed to "abnormal" for further training of the ANN (125) for direct recognition of the anomaly (e.g., instead of relying upon deviation from known "normal" clusters for an inference of anomaly).

Thus, the ANN (125) can be trained to identify abnormal sensor data and estimate the degree of severity in anomaly to schedule a maintenance service.

Figure 6:
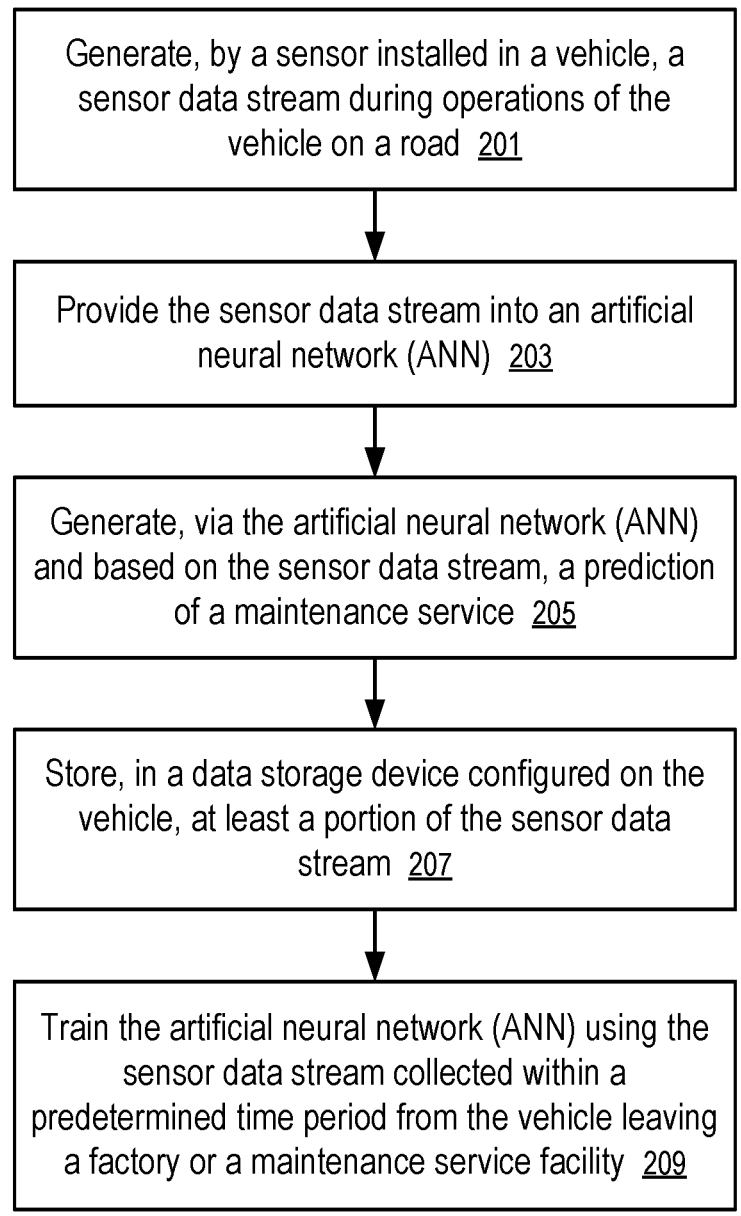
FIG. 6 shows a method of predictive maintenance according to one embodiment.

FIG. 6 shows a method of predictive maintenance according to one embodiment. For example, the method of FIG. 6 can be implemented in the data storage device (101) of FIG. 1 or 2 in the vehicle (111) or in a computer system (131) in the vehicle (111) of FIG. 2.

At block 201, a sensor (e.g., 103) installed in a vehicle (111) generates a sensor data stream (e.g., 121) during operations of the vehicle (111) on a road (102).

At block 203, the sensor data stream (e.g., 121) is provided into an artificial neural network (ANN) (125). For example, the ANN (125) can include a spiking neural network (SNN).

At block 205, the artificial neural network (ANN) (125) generates, based on the sensor data stream (e.g., 121), a prediction of a maintenance service.

At block 207, a data storage device (101) configured on the vehicle stores at least a portion of the sensor data stream (e.g., 121).

At block 209, the artificial neural network (ANN) is trained using the sensor data stream (e.g., 121) collected within a predetermined time period from the vehicle leaving a factory or a maintenance service facility (127).

For example, the artificial neural network (ANN) can be configured to identify a component of the vehicle (111) that needs repair or replacement in the maintenance service and/or identify a predicted time period to failure or malfunctioning of the component, or a suggested time period to a recommended maintenance service of the component prior the failure or malfunctioning of the component. Thus, the performance of the predicted maintenance service can avoid an incident of failure or malfunctioning of the component while the vehicle (111) operates on the road (102).

For example, the sensor (103) can be a microphone mounted in vicinity of the component, a vibration sensor attached to the component, a pressure sensor installed in the component, a force or stress sensor mounted on or attached to the component, a deformation sensor attached to the component, an accelerometer configured to measure motion parameters of the component.

Optionally, the data storage device (101), the computer system (131) of the vehicle (111), and/or a server (119) remote from the vehicle can have a machine learning module configured to train the artificial neural network (ANN) (125) during a period of time in which the vehicle (111) is assumed to be in a healthy state, such as a predetermined time period from the vehicle (111) leaving a factory or a maintenance service facility (127).

For example, the machine learning module can use an unsupervised machine learning (175) to train the ANN (125) to recognize/classify normal patterns of sensor data (121) and thus to have the capability to detect anomaly based on deviation from the normal patterns, as illustrated in FIG. 4. Alternatively, supervised machine learning (171) can be used, as illustrated in FIG. 3 or 5.

For example, unsupervised machine learning (175) can be applied by the data storage device (101) or the computer system (131) of the vehicle (111) during the predetermined period of time in which the vehicle and/or the component is known to be operating without troubles or degradations.

Alternatively, or in combination, some of the sensor data (121) stored in the data storage device (101) of the vehicle (111) can be uploaded to the server (119) for training the ANN (125).

In at least some embodiments disclosed herein, the data storage device (101) is configured to accelerate the computations of the artificial neural network (ANN) (125) of the vehicle (111).

For example, in addition to the typical operations to support data access and storage, the data storage device (101) can be further configured to perform at least part of the computations involving the artificial neural network (ANN) (125), such as the generation of the predictions (e.g., 129 or 173) or classifications (e.g., 179) from the sensor data (121) and/or the adjustment of the ANN (125) through unsupervised machine learning (175) (e.g., as illustrated in FIG. 4) and/or supervised machine learning (171) (e.g., as illustrated in FIG. 3 or 5).

For example, the computations configured in the data storage device (101) can be used to reduce the amount of data to be transmitted to the processor(s) (133) to use or apply the ANN (125) and/or reduce the computation tasks of the processor(s) (133) in evaluating the outputs of the ANN (125) and/or in training the ANN (125). Such an arrangement can result in faster output from the data storage device (101) and/or lower energy usage, since the data would not have to be moved in and out of the memory to a dedicated, standalone neural network accelerator. The computation capability of the data storage device (101) in processing data related to the ANN (125) enables the computer system (131) of the motor vehicle (111) to monitor the health of the automotive components (e.g., in a non-real-time manner, or a pseudo-real-time manner), with reduced impact, or no impact, on the processing of mission critical tasks (e.g., autonomous driving by the ADAS (105)). Further, the computation capability of the data storage device (101) can be used to accelerate the processing of the sensor data for ADAS (105) and thus improve the processing of mission critical tasks.

Figure 7:
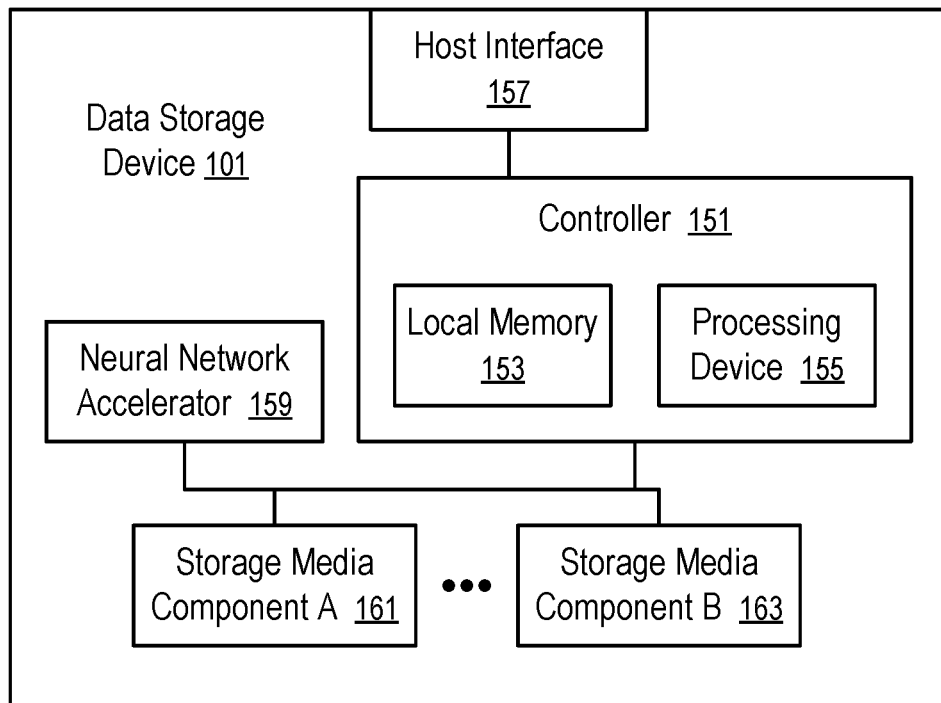
FIG. 7 shows a data storage device to accelerate neural network computations according to one embodiment.

FIG. 7 shows a data storage device (101) to accelerate neural network computations according to one embodiment. For example, the data storage device (101) of FIG. 7 can be used to implement the data storage device (101) of the vehicle (111) illustrated in FIG. 1 or 2.

In FIG. 7, the data storage device (101) has a host interface (157) configured to communicate with a processor (e.g., 133). For example, the communication between the processor (e.g., 133) and the host interface (157) can be, at least in part, in accordance with a communication protocol for a peripheral component interconnect express (PCIe) bus, a serial advanced technology attachment (SATA) bus, a universal serial bus (USB) bus, and/or a storage area network (SAN).

For example, the host interface (157) can be used to receive sensor data (121) generated by the sensors (103) of the vehicle (111) to optionally store a portion of the sensor data (121) in the storage media components (161 to 163).

For example, each of the storage media components (161 to 163) can be a memory integrated circuit configured to store data. For example, a media component (161 or 163) can include one or more integrated circuit dies embedded in an integrated circuit package. An integrated circuit die can have many memory units formed thereon to store data.

In general, some memory integrated circuits are volatile and require power to maintain the stored data; and some memory integrated circuits are non-volatile and can retain the stored data even when not powered.

Examples of non-volatile memory include flash memory, memory units formed based on negative-and (NAND) logic gates, negative-or (NOR) logic gates, phase-change memory (PCM), magnetic memory (MRAM), resistive random-access memory, cross point storage and memory devices. A cross point memory device uses transistor-less memory elements, each of which has a memory cell and a selector that are stacked together as a column. Memory element columns are connected via two perpendicular lays of wires, where one lay is above the memory element columns and the other lay below the memory element columns. Each memory element can be individually selected at a cross point of one wire on each of the two layers. Cross point memory devices are fast and non-volatile and can be used as a unified memory pool for processing and storage. Further examples of non-volatile memory include Read-Only Memory (ROM), Programmable Read-Only Memory (PROM), Erasable Programmable Read-Only Memory (EPROM) and Electronically Erasable Programmable Read-Only Memory (EEPROM) memory, etc. Examples of volatile memory include Dynamic Random-Access Memory (DRAM) and Static Random-Access Memory (SRAM).

The data storage device (101) can have a controller (151) that includes volatile local memory (153) and at least one processing device (155).

The local memory of the controller (151) can be an embedded memory configured to store instructions for performing various processes, operations, logic flows, and routines that control operation of the processing device (155), including handling communications between the data storage device (101) and the processor(s) (e.g., 133) of the vehicle (111), and other functions described herein. The local memory (151) of the controller (151) can include read-only memory (ROM) for storing micro-code and/or memory registers storing, e.g., memory pointers, fetched data, etc., and/or volatile memory, such as Dynamic Random-Access Memory (DRAM) and Static Random-Access Memory (SRAM).

In FIG. 7, the data storage device (101) includes a neural network accelerator (159) coupled to the controller (151) and/or the storage media components (161 to 163).

For example, the neural network accelerator (159) can be configured to perform matrix arithmetic computations. The computations involving ANN (125) have matrix multiplication and accumulation operations, which can be computational intensive for a generic processor (e.g., 133). Using the neural network accelerator (159) to perform the matrix arithmetic computations can reduce the data to be transmitted to the processor(s) (133) of the vehicle (111) and reduce the computation workload for the processor(s) (133).

For example, when the ANN (125) includes a spiking neural network (SNN), the simulation of the differential equation(s) for controlling the activation level of SNN neurons can be computationally intensive for a generic processor (e.g., 133). The neural network accelerator (159) can use special hardware to simulate the differential equation(s) and thus improve the computational efficiency of the computer system (131) as a whole.

In some implementations, the neural network accelerator (159) is an integrated circuit device separate from the controller (151) and/or the storage media components (161 to 163). Alternatively, or in combination, a neural network accelerator (159) is integrated with the controller (151) in an integrated circuit package. Further, a neural network accelerator (159) can be integrated in at least one of the storage media components (161 to 163), as illustrated in FIG. 8.

Figure 8:
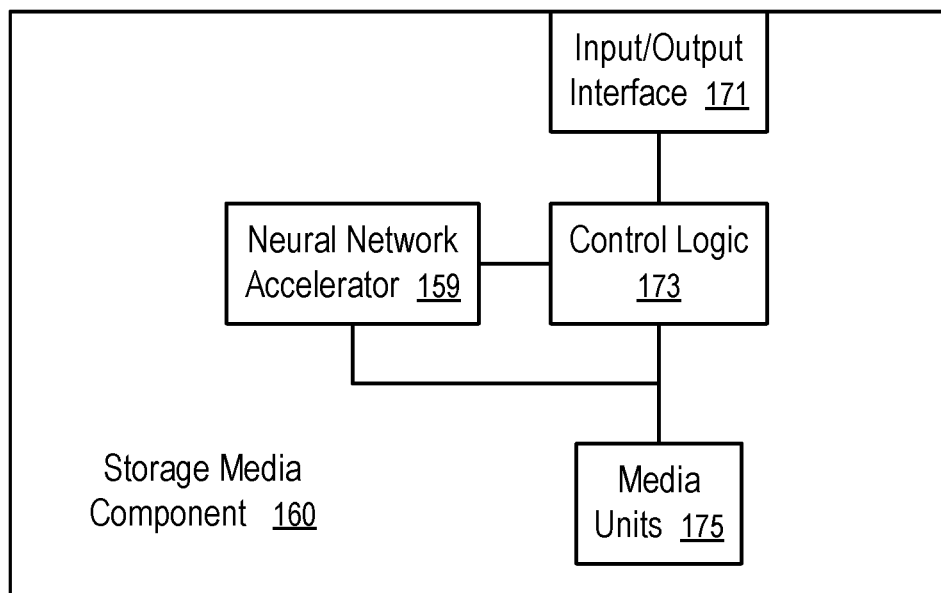
FIG. 8 shows a storage media component to accelerate neural network computations according to one embodiment.

FIG. 8 shows a storage media component (160) to accelerate neural network computations according to one embodiment. For example, each or some of the storage media components (161 to 163) in FIG. 7 can be implemented using a storage media component (160) of FIG. 8.

In FIG. 8, the storage media component (160) can be housed within an integrated circuit package. An input/output (I/O) interface (171) of the storage media component (160) is configured to process input/output signals in the pins of the integrated circuit package. For example, the input/output signals can include address signals to specify locations in the media units (175) and data signals representing data to be written in the media units (175) at the locations specified via the address signals, or data retrieved from the locations in the media units (175).

In FIG. 8, a neural network accelerator (159) is coupled with the control logic (173) and/or the media units (175) to perform computations that are used in the evaluation of the output of an ANN (125) and/or in the training of the ANN (125).

For example, the input/output interface (171) can receive addresses that identify matrices that are stored in the media units and that are to be operated upon via the neural network accelerator (159). The storage media component (160) can provide the computation results of the neural network accelerator (159) as the output data responsive to the addresses, store the output data in a buffer for further operations, store the output data into a location in the media units (175) specified via the address signals. Thus, the computations performed by the neural network accelerator (159) can be within the storage media component (160), which is close to the media units (175) in which the matrix data is stored. For example, each of the media units (175) can be an integrated circuit die on which memory units of non-volatile memory are formed.

For example, the state data of SNN neurons can be stored in the media units (175) according to a predetermined pattern. The neural network accelerator (159) can automatically update the states of the SNN neurons according to the differential equation(s) for controlling the activation level of SNN neurons over time. Optionally, the neural network accelerator (159) is configured to processing spiking of neurons in the neural network. Alternatively, the neural network accelerator (159) of the data storage device (101) and/or the processor(s) (133) can be configured to process the spiking of neurons and/or accumulation of inputs to the SNN.

Figure 9:
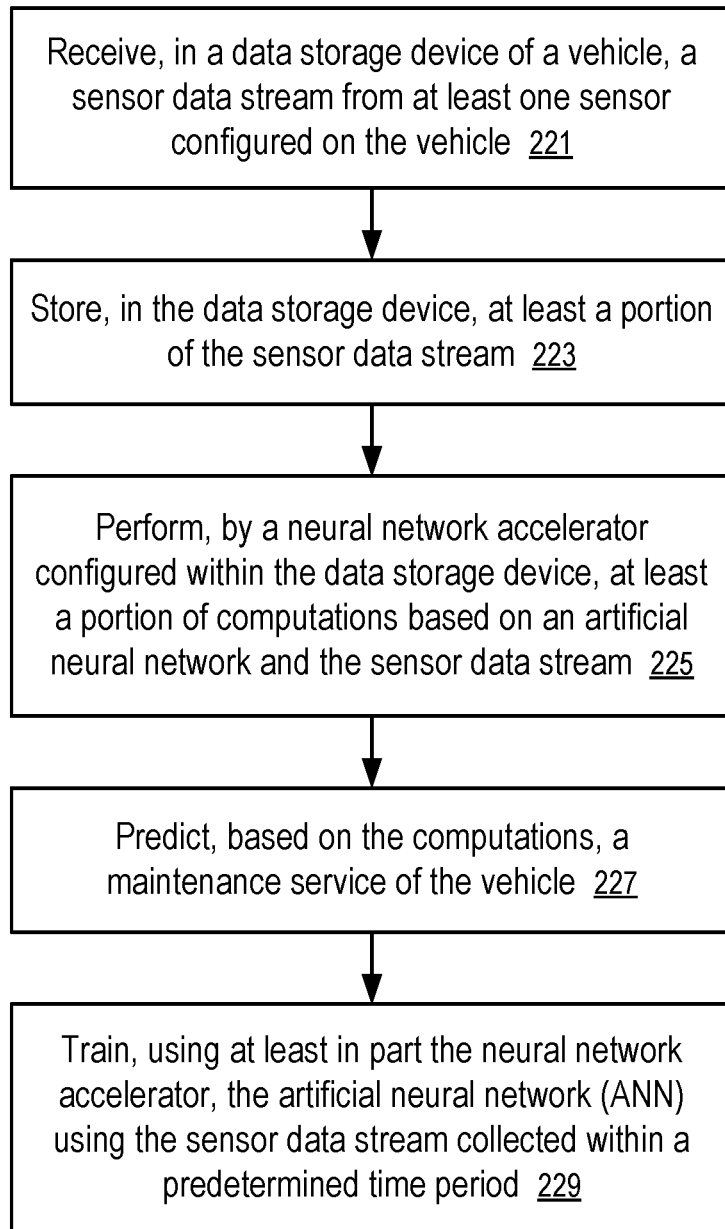
FIG. 9 shows a method to accelerate neural network computations in motor vehicles according to one embodiment.

FIG. 9 shows a method to accelerate neural network computations in motor vehicles according to one embodiment. For example, the method of FIG. 9 can be implemented in a vehicle (111) of FIG. 1 or 2 using a data storage device (101) of FIG. 7 and/or a storage media component (160) of FIG. 8. For example, the method of FIG. 9 can be used in combination with the method of FIG. 6.

At block 221, a data storage device (101) of a vehicle (111) receives a sensor data stream from at least one sensor (e.g., 103) configured on the vehicle (111).

At block 223, the data storage device (101) stores at least a portion of the sensor data stream.

At block 225, a neural network accelerator (159) configured within the data storage device (101) performs at least a portion of computations based on an artificial neural network (125) and the sensor data stream.

At block 227, a maintenance service of the vehicle (111) is predicted based at least in part on the computations performed by the neural network accelerator (159) configured within the data storage device (101).

Optionally, at block 229, the artificial neural network (ANN) is trained in the vehicle (111), using at least in part the neural network accelerator and using the sensor data stream collected within a predetermined time period, such as a period following the delivery of the new vehicle (111) from a factory or following the replacement of a component in a maintenance service facility (127).

For example, the neural network accelerator (159) can be configured on an integrated circuit device that is separate from a controller (151) of the data storage device and/or separate from the storage media components (161 to 163).

For example, the neural network accelerator (159) can be configured on an integrated circuit device that includes a controller (151) of the data storage device (101), or on an integrated circuit device that includes storage media component (160, 161 or 163) of the data storage device (101).

For example, the neural network accelerator (159) can be configured to perform computations, such as matrix arithmetic computations for ANN and/or or differential equation simulations for SNN, using data stored in the data storage device (101).

Examples of the matrix arithmetic computations include matrix multiplication and accumulation operations. After a computation to generate a result of the matrix arithmetic computations using a data stored in the data storage device (101), the neural network accelerator (159) can provide the result as output of the data storage device (111) in retrieving data (e.g., in response to a read command). Alternatively, or in combination, the result of the matrix arithmetic computation can be buffered in the data storage device (101) as operand for a next matrix computation performed in combination with a matrix of data retrieved from the non-volatile memory via a read command received in the host interface (157).

When the artificial neural network (ANN) (125) includes a spiking neural network (SNN), the neural network accelerator can be configured to simulate a differential equation controlling activation levels of neurons in the spiking neural network (SNN). Optionally, the storage media component is configured to store states of the neurons in the spiking neural network according to a predetermined pattern; and the neural network accelerator is configured to automatically update the states of the neurons over time according to the differential equation. For example, the neural network accelerator (159) can be configured to train the spiking neural network (SNN) via unsupervised machine learning to detect anomaly.

The computations performed by the neural network accelerator (159) according to an artificial neural network (ANN) (125) involve different types of data that have different patterns of usages of the data storage device (101).

For example, making a prediction using the artificial neural network (ANN) (125) includes the use of data specifying the model of the artificial neural network (ANN) (125), input data provided to the artificial neurons, and output data generated by the artificial neurons.

The storage capacity of the data storage device (101) can be partitioned into different portions for the different types of ANN-related data. The different portions can be separately configured to optimize the access and storage of the corresponding data according to their patterns of usages by the neural network accelerator (159) and/or the processor(s) (133) of the computer system (131) in which the data storage device (101) is configured.

The model of the artificial neural network (ANN) (125) can include the parameters specifying the static attributes of individual artificial neurons in the ANN (125) and the neuron connectivity in the ANN (125). The model data of the ANN (125) is static and does not change during the prediction calculation made using the ANN (125). Thus, the usage pattern of the model data is mostly read. However, the model data of the ANN (125) can change when an updated ANN (125) is installed. For example, the vehicle (111) can download an updated ANN (125) from the server (119) to the data storage device (101) of the vehicle (111) to update its prediction capability. The model data of the ANN (125) can also change during or after the training of the ANN (125) using a machine learning technique (e.g., 171 or 175). It is preferred to configure a separate partition or namespace of the data storage device (101) to store the model data, where the partition or namespace is operated according to configuration parameters that optimize the memory units for the specific usage patterns of the model data (e.g., mostly read, infrequent update). For example, when the memory units are implemented using a flash memory based on NAND logic gates, the memory units in the ANN model partition/namespace can be configured to operate in a multi-level cell (MLC) mode, a triple level cell (TLC) mode, or a quad-level cell (QLC) mode, wherein each memory cells stores two, three, or four bits for increased storage capability.

Input data provided to the artificial neurons in the ANN (125) can include external inputs and internal inputs. The external inputs are generated typically by the sensors (103) of the vehicle (111) but not by artificial neurons in the ANN (125). The external inputs can be saved in a cyclic fashion so that the input data of the most recent time period of a predetermined length of driving can be found in the data storage device (101). Thus, it is preferred to configure a separate partition or namespace of the data storage device (101) to store the external input data, where the partition or namespace is operated according to configuration parameters that optimize the memory units for the storage pattern of the external input data (e.g., enhanced endurance, cyclic overwrite). For example, when the memory units are implemented using a flash memory based on NAND logic gates, the memory units in the ANN input partition/namespace can be configured to operate in a single level cell (SLC) mode, where each memory cell stores one bit of data for improved endurance in cyclic overwriting operations.

In some implementations, artificial neurons can have state variables that change over time in response to inputs during prediction calculations. For example, the activation level of a spiking neuron can change over time and is considered a dynamic state variable of the spiking neuron. In some implementations, such state variable data of artificial neurons has a similar storage usage pattern as the external input data; and thus, the state variable data can be stored in the partition or namespace configured for the external input data. In other implementations, the state variable data of artificial neurons is kept in a buffer and stored less frequently than the external inputs; and thus, another partition/namespace can be configured for storing the dynamic state variable data of artificial neurons.

Output data generated by the artificial neurons in the ANN (125) can be buffered for further access by the neural network accelerator (159) and/or the processor(s) (133) of the computer system (131). The output data can include external outputs and internal outputs. The external inputs are generated by artificial neurons as the output from the ANN (125), such as the results of classifications or predictions made by the ANN (125). The output of the ANN (125) is typically further processed by the processor(s) (133) of the computer system (131). The external inputs may be saved periodically (e.g., in a way similar to the storing of the state variable data). The internal outputs and/or some of the external outputs can be internal inputs to artificial neurons in the ANN (125). In general, it may not be necessary to store the internal outputs from the buffer of the data storage device to the storage media components. In some implementations, when the buffer capability of the data storage device (101) is insufficient to hold the entire state variable data and/or the internal outputs, the data storage device (101) can use a swap partition/namespace to extend the capacity of the buffer. The swap partition/namespace can be configured for optimized random access and for improved endurance.

External outputs and/or dynamic states of neurons can be saved in a separate output partition or namespace, in a cyclic way so that the external output data and/or dynamic states of the neurons can be periodically stored, and the most recent sets of the external outputs and/or dynamic states can be found in the data storage device (101). External outputs and/or dynamic states of neurons can be stored selectively, since some of such data can be re-generated by the ANN from the external inputs stored in the input partition or namespace. Preferably, the output partition or namespace is configured to store one or more sets of external outputs and/or dynamic states that cannot be created from the external inputs stored in the input partition or namespace. In storing data in a cyclic way in an input/output partition or namespace, the oldest stored data sets are erased to make rooms for the most recent data sets. The ANN input/output partition/namespace can be configured for an optimized sequential write stream for copying data from the buffer of the data storage device into the memory units in the storage media components of the data storage device.

Figure 10:
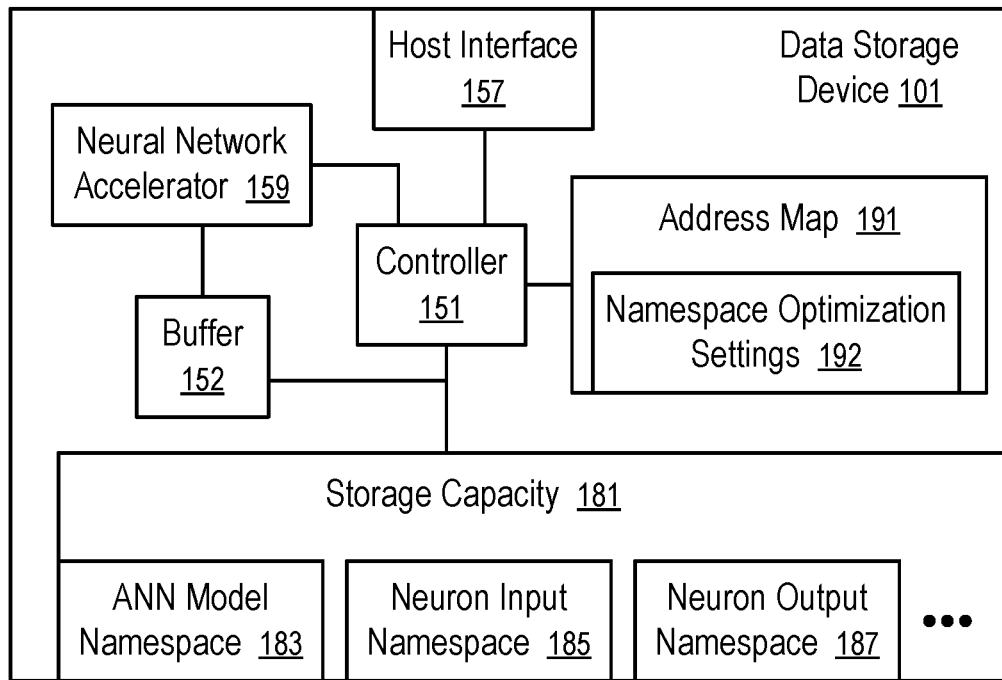
FIG. 10 shows a data storage device configured to support neural network computations according to one embodiment.

FIG. 10 shows a data storage device (101) configured to support neural network computations according to one embodiment. For example, the data storage device (101) can be used in the vehicle (111) in FIG. 1 or 2 to facilitate predictive maintenance and/or support the ADAS (105).

The data storage device (101) of FIG. 10 includes a host interface (157) and a controller (151), similar to the data storage device (101) of FIG. 7.

The storage capacity (181) of the data storage device (101) of FIG. 10 can be implemented using a set of storage media components, similar to the storage media components (161 to 163) in the data storage device (101) of FIG. 7.

A set of namespaces (183, 185, 187, . . . ) can be created on the storage capacity (181) of the data storage device (101). Each of the namespace (e.g., 183, 185, or 187) corresponds to a named portion of the storage capacity (181). Logical addresses are defined within each namespace. An address map (191) is configured to map between the logical addresses defined in the namespaces (183, 185, 187, . . . ) to the physical addresses of memory units in the storage media components (e.g., 161 to 163 illustrated in FIG. 7).

The address map (191) can include namespace optimization settings (192) for the namespaces (183, 185, and 187).

For example, an ANN model namespace (183) can be a memory/storage partition configured for the model data of the artificial neural network (ANN) (125). The namespace optimization settings (192) optimizes the memory operations in the ANN model namespace (183) according to the data usage pattern of ANN models (e.g., mostly read, infrequent update centric).

For example, a neuron input namespace (185) can be a memory/storage partition configured for the external input data to the artificial neural network (ANN) (125). The namespace optimization settings (192) optimizes the memory operations in the neuron input namespace (185) according to the data usage pattern of the external input data (e.g., for enhanced endurance supporting cyclic overwrite of continuous input data flow for sequential writes).

For example, a neuron output namespace (187) can be a memory/storage partition/configured for the external output data provided from the artificial neural network (ANN) (125). The namespace optimization settings (192) optimizes the memory operations in the neuron output namespace (187) according to the data usage pattern of the external output data (e.g., improved endurance for periodically overwrite of data with random read/write access).

The data storage device (101) includes a buffer (152) configured to store temporary/intermediate data of the artificial neural network (ANN) (125), such as the internal inputs/outputs of the artificial neurons in the ANN (125).

Optionally, a swap namespace can be configured in the storage capacity (181) to extend the capacity of the buffer (152).

Optionally, the address map (191) includes a mapping between logic memory addresses received in the host interface (157) to access data of artificial neurons and the identities of the artificial neurons. Thus, a read or write command to access one type of data of an artificial neuron in one namespace can cause the controller 151 to access another type of data of the artificial neuron in another namespace.

For example, in response to a request to write external input data for a neuron into the storage capacity (181) of the data storage device (185), the address map (191) can be used to calculate the addresses of the model parameters of the neuron in the ANN model namespace (183) and read the model parameters into the buffer (152) to allow the neural network accelerator (159) to perform the computation of the output of the neuron. The output of the neuron can be saved in the buffer (152) as the internal input to other neurons (e.g., to reduce write amplification). Further, the identities of the other neurons connected to the neuron can also be retrieved from the ANN model namespace (183) into the buffer (152), which allows the neural network accelerator (159) and/or the processor to further process the propagation of the output in the ANN (125). The retrieval of the model data from the ANN model namespace (183) can be performed in parallel with the storing of the external input data into the neuron input namespace (185). Thus, the processors (133) of the computer system (131) of the vehicle (111) do not have to explicitly send in read commands for the retrieval of the model data from the ANN model namespace (183).

Similarly, in response to reading output data of a neuron, the address map (191) can be used to compute the addresses of the model parameters of the neuron stored in the ANN model namespace (183) and read the model parameters into the buffer (152) to allow the neural network accelerator (159) to apply internal inputs in the buffer (152) to the perform the computation of the output of the neuron. The computed output can be provided as a response to the reading of the output data for the neuron, without the data storage device (101) having to store the output data in the storage media components (e.g., 161 to 163). Thus, the processors (133) and/or the neural network accelerator (159) can control the computations of the neuron via writing inputs to neurons and/or reading outputs from neurons.

In general, incoming external input data to the ANN (125) can be raw sensor data (121) generated directly by the sensors (103) without processing by the processors (133) and/or the neural network accelerator (159). Alternatively, indirect sensor data (121) that has processed by the processors (133) for the ANN (125) from the signals from the sensors (103) can be provided as the external input data. The incoming external input data can be accepted in the host interface (157) and written in a cyclic way into the neuron input namespace (185), and automatically buffered in the buffer (152) for neural network accelerator (159) to generate neuron outputs using the model stored in the ANN model namespace (183). The outputs generated by the neural network accelerator (159) can be further buffered as internal inputs for further application of the model in the ANN model namespace (183). When the external outputs become available, the data storage device (101) can report the completion of the write requests with an indication of the availability of the external outputs. Optionally, the controller 151 and/or the neural network accelerator (159) can generate internal read commands to propagate signals in the ANN (125) in generating the external outputs. Alternatively, the host processors (133) can control the propagation of signals in the ANN (125) by selectively reading outputs of neurons; and the data storage device (101) can actively buffer data that may be needed in the buffer (152) to accelerate the ANN computation.

Figure 11:
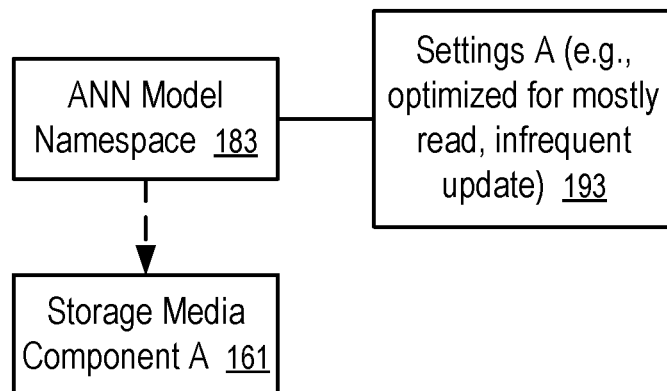
FIG. 11 illustrates the configuration of a namespace for an artificial neural network (ANN) model according to one embodiment.

FIG. 11 illustrates the configuration of a namespace (183) for an artificial neural network (ANN) model according to one embodiment. For example, the configuration of FIG. 11 can be implemented in the data storage device (101) illustrated in FIGS. 7 and/or 10. For example, the settings (193) of FIG. 11 can be part of the namespace optimization settings (192) of FIG. 10.

The configuration of FIG. 11 maps an ANN model namespace (183) to at least one storage media component A (161). Preferably, the at least one storage media component A (161) can be used by the controller (151) in parallel with storage media components (e.g., 163) that hosts the other namespaces (e.g., 185 and 187) of ANN data. For example, the storage media component A (161) can be in an integrated circuit package that is separate from the integrated circuit packages for the other namespaces (e.g., 185 and 187). Alternatively, the storage media components (161 to 163) are formed on separate integrated circuit dies embedded in a same integrated circuit package. Alternatively, the storage media components (161 to 163) can be formed on separate regions of an integrated circuit die, where the separate regions can be operated substantially in parallel (e.g., for read, for erase, and/or for write).

In FIG. 11, the settings (197) are optimized to the usage pattern of mostly read and infrequent update.

Figure 12:
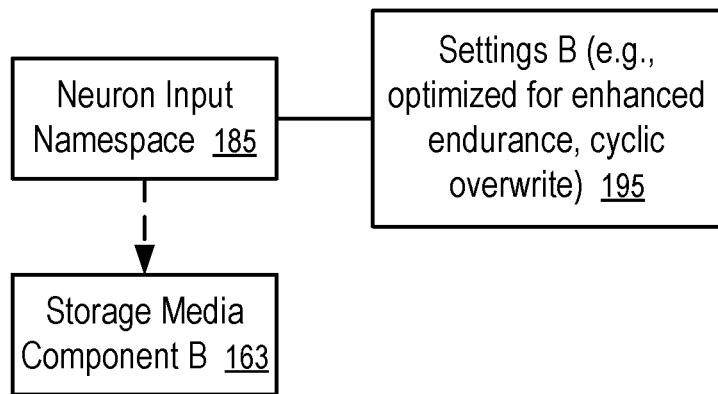
FIG. 12 illustrates the configuration of a namespace for the inputs to artificial neurons according to one embodiment.

FIG. 12 illustrates the configuration of a namespace (185) for the inputs to artificial neurons according to one embodiment. For example, the configuration of FIG. 11 can be implemented in the data storage device (101) illustrated in FIGS. 7 and/or 10. For example, the settings (195) of FIG. 11 can be part of the namespace optimization settings (192) of FIG. 10.

The configuration of FIG. 12 maps a neuron input namespace (185) to at least one storage media component B (163). Preferably, the at least one storage media component B (163) can be used by the controller (151) in parallel with storage media components (e.g., 161) that hosts the other namespaces (e.g., 183 and 187) of ANN data. For example, the storage media component B (163) can be in an integrated circuit package that is separate from the integrated circuit packages for the other namespaces (e.g., 183 and 187). Alternatively, the storage media components (161 to 163) are formed on separate integrated circuit dies embedded in a same integrated circuit package. Alternatively, the storage media components (161 to 163) can be formed on separate regions of an integrated circuit die, where the separate regions can be operated substantially in parallel (e.g., for read, for erase, and/or for write).

In FIG. 12, the settings (197) are optimized to the usage pattern of enhanced endurance in cyclic sequential overwrite in recording a continuous stream of input data that is sampled at a fixed time interval.

Figure 13:
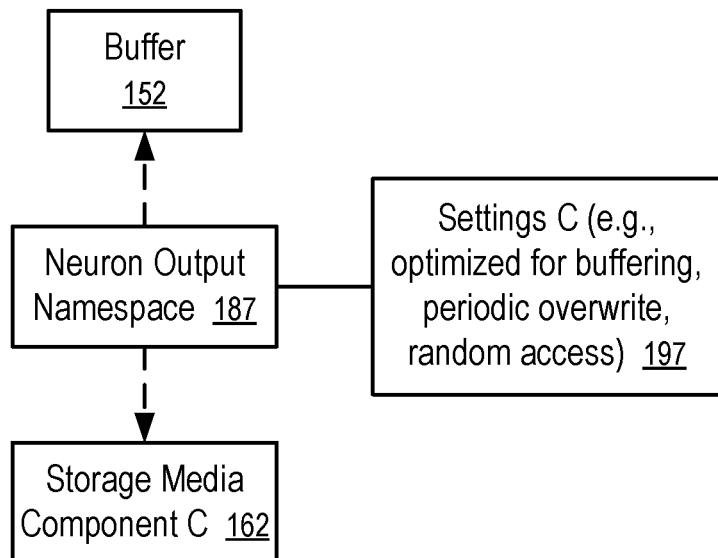
FIG. 13 illustrates the configuration of a namespace for the outputs from artificial neurons according to one embodiment.

FIG. 13 illustrates the configuration of a namespace (187) for the outputs from artificial neurons according to one embodiment. For example, the configuration of FIG. 11 can be implemented in the data storage device (101) illustrated in FIGS. 7 and/or 10. For example, the settings (197) of FIG. 11 can be part of the namespace optimization settings (192) of FIG. 10.

The configuration of FIG. 13 maps a neuron output namespace (187) to at least one storage media component C (162). Preferably, the at least one storage media component C (162) can be used by the controller (151) in parallel with storage media components (e.g., 161 and 163) that hosts the other namespaces (e.g., 183 and 185) of ANN data. For example, the storage media component C (162) can be in an integrated circuit package that is separate from the integrated circuit packages for the other namespaces (e.g., 183 and 185). Alternatively, the storage media components (161 to 163) are formed on separate integrated circuit dies embedded in a same integrated circuit package. Alternatively, the storage media components (161 to 163) can be formed on separate regions of an integrated circuit die, where the separate regions can be operated substantially in parallel (e.g., for read, for erase, and/or for write).

In FIG. 13, the settings (197) are optimized to the usage pattern of buffered data for periodic overwrite with random access. For example, memory units are configured via the optimization settings (193 to 197) to update/overwrite in the neuron output namespace (187) at a frequency higher than in the ANN model namespace (183), but lower than in the neuron input namespace (185).

Figure 14:
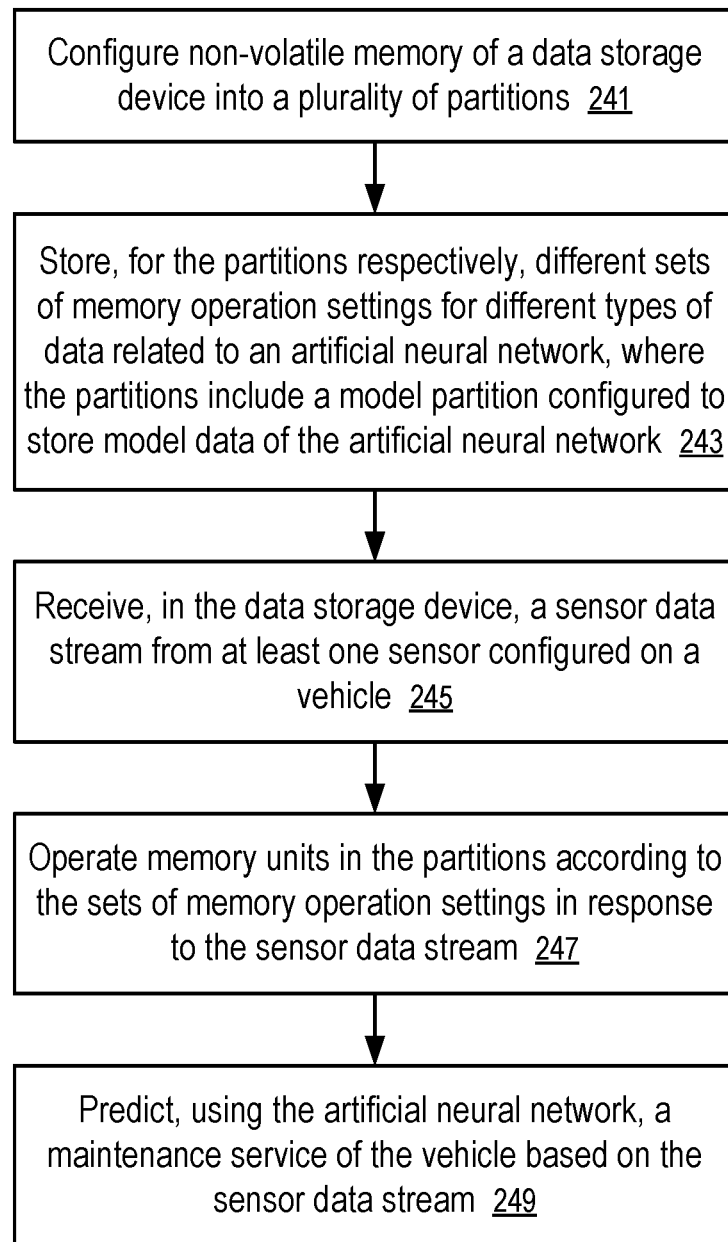
FIGS. 14-16 show methods of predictive maintenance supported by a model partition, an input partition and an output partition according to one embodiment.

FIG. 14 shows a method of predictive maintenance supported by a model partition according to one embodiment. For example, the method of FIG. 14 can be implemented in a vehicle (111) of FIG. 1 or 2 using a data storage device (101) of FIG. 7 or 10 and/or a storage media component (160) of FIG. 8. For example, the method of FIG. 14 can be used in combination with the method of FIGS. 6 and/or 9.

At block 241, non-volatile memory of a data storage device (101) is configured into a plurality of partitions (e.g., 183, 185, 187, . . . ). For example, the non-volatile memory can have the same type of memory units for storing data (e.g., NAND flash memory units); and the same type of memory units in the different partitions (e.g., 183 to 187) can be configured differently to optimize their performances according to the usage patterns of the data stored in the different partitions (e.g., 183 to 187).

At block 243, the data storage device (101) stores, for the partitions (e.g., 183, 185, 187, . . . ) respectively, different sets of memory operation settings (e.g., 193, 195, 197) for different types of data related to an artificial neural network (125), where the partitions (e.g., 183, 185, 187, . . . ) include a model partition (e.g., 193) configured to store model data of the artificial neural network (125).

At block 245, the data storage device (101) receives a sensor data stream (e.g., 121) from at least one sensor (103) configured on a vehicle (111).

At block 247, a controller (151) of the data storage device (101) operates memory units in the partitions (183, 185, 187, . . . ) according to the sets of memory operation settings (e.g., 193, 195, 197) in response to the sensor data stream (e.g., 121).

At block 249, the computer system (131) having the data storage device (101) predicts, using the artificial neural network (125), a maintenance service of the vehicle (111) based on the sensor data stream (e.g., 121).

For example, the memory operation settings configure the model partition (e.g., 183) to store three or more bits per memory cell. The memory operating settings can include address map (191) to map between neurons in the ANN (125) and inputs to the neurons. When a first address of an input to a neuron in the artificial neural network (125) is received, the first address in an input partition (e.g., 185) separate from the model partition (e.g., 183) can be converted into at least one second address of model data associated with the neuron, such that the attributes of the neuron and the identities of neurons connected to the neuron can be retrieved from the model partition (e.g., 183) without an explicit command from the processors (133). The controller (151) can automatically retrieve, from the model partition (e.g., 183), the model data associated with the neuron using the at least one second address, in response to the receiving of the first address. A neural network accelerator (159) can generate an output of the neuron from the input to the neuron and the model data associated with the neuron. In general, input to the neuron can include outputs from multiple neurons that are connected to the neuron in the ANN (125). The controller (151) can save the output of the neuron in the buffer (152) in the data storage device (101) to facilitate accelerated access to the output by the host processor(s) (133) and/or the neural network accelerator (159).

Typically, the model data does not change during computation to predict the maintenance service. For example, the model data can include neuron connectivity data of the artificial neural network and static attributes of neurons in the artificial neural network. The memory operation settings (e.g., 192) can configure the model partition (e.g., 183) to store more than one bit per memory cell in the non-volatile memory based on the usage pattern of mostly read, infrequent update of the model data.

For example, the partitions (e.g., 183, 185, 187, . . . ) in the data storage devices can be implemented as namespaces in which logical addresses are defined; and an address map (191) in the data storage device is configured to map the namespaces (183, 185, 187, . . . ) to separate storage media components (e.g., 161, 163, 162, . . . ).

The model data in the model namespace (183) is updatable during training via machine learning (171 or 175), or during over-the-air update of the ANN (125) from the server (119).

In some implementations, the controller (151) is configured, via the address map (191) to retrieve, from the model partition, model data associated with a neuron in the artificial neural network, in response to an input to, or an output from, the neuron being addressed in a partition separate from the model partition (183). Further, the controller (151) can retrieve, from the model partition (183), the model data associated with the neuron in parallel with storing input to the neuron in the partition (e.g., 185) that is separate from the model partition (183).

Figure 15:
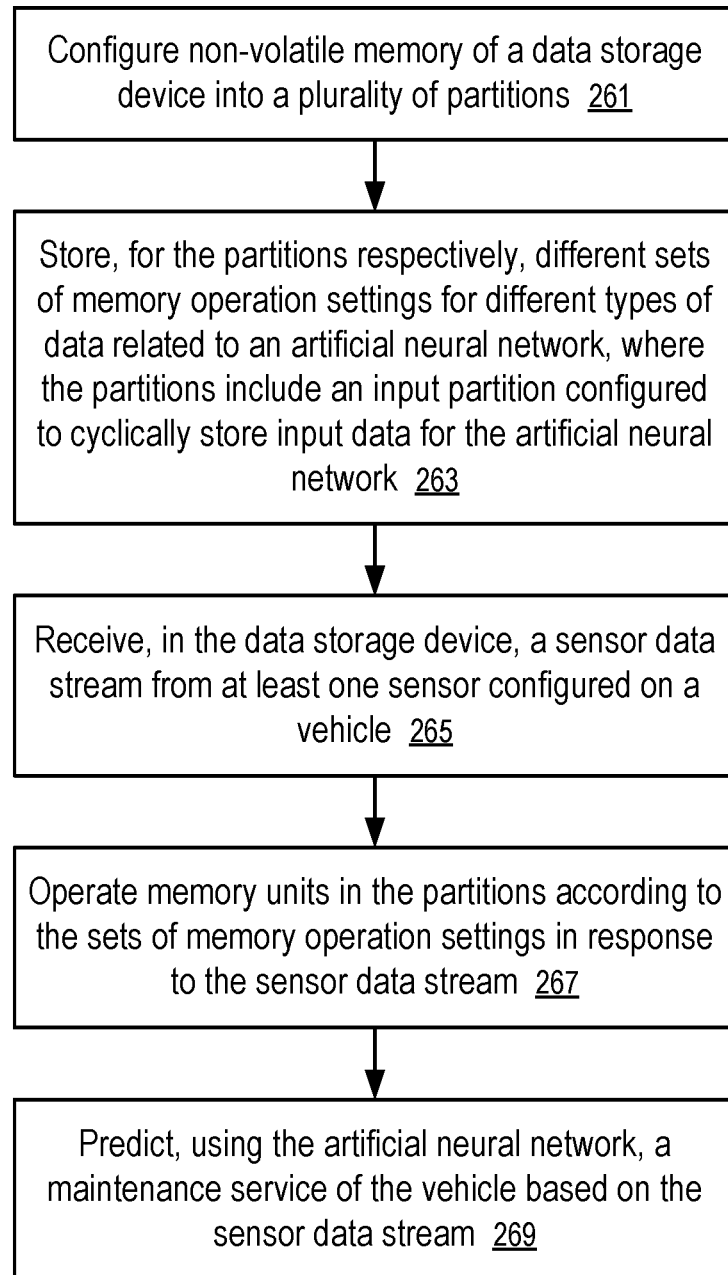

FIG. 15 shows a method of predictive maintenance supported by an input partition according to one embodiment. For example, the method of FIG. 15 can be implemented in a vehicle (111) of FIG. 1 or 2 using a data storage device (101) of FIG. 7 or 10 and/or a storage media component (160) of FIG. 8. For example, the method of FIG. 15 can be used in combination with the method of FIGS. 6, 9, and/or 14.

At block 261, non-volatile memory of a data storage device (101) is configured into a plurality of partitions (e.g., 183, 185, 187, . . . ). For example, the non-volatile memory can have the same type of memory units (e.g., NAND flash memory units) implemented in multiple storage media components (e.g., 161 to 163).

At block 263, the data storage device (101) stores, for the partitions (e.g., 183, 185, 187, . . . ) respectively, different sets of memory operation settings (e.g., 193, 195, 197) for different types of data related to an artificial neural network (125), where the partitions (e.g., 183, 185, 187, . . . ) include an input partition (e.g., 185) configured to cyclically store input data for the artificial neural network (125).

For example, the input partition (185) can be configured to store external inputs for the artificial neural network (125) but not internal inputs. The input data stored in the input partition (185) is independent of outputs from neurons in the artificial neural network (125).

For example, the input data stored in the input partition (185) can include a portion of the sensor data stream (e.g., 121). In some embodiments, the input data stored in the input partition (185) is computed from the sensor data stream (e.g., 121) for a subset of neurons in the artificial neural network (125).

For example, the memory operation settings (e.g., 195) configure the input partition (185) to store one bit per NAND memory cell in the non-volatile memory for enhanced endurance for repeated data erasure and data programming.

For example, the memory operation settings (e.g., 195) configure the controller to write sequentially the input data into to the input partition (185), and to overwrite oldest input data in the input partition (185) with the most recent input data received in the data storage device (101).

At block 265, the data storage device (101) receives a sensor data stream (e.g., 121) from at least one sensor (103) configured on a vehicle (111).

At block 267, a controller (151) of the data storage device (101) operates memory units in the partitions (183, 185, 187, . . . ) according to the sets of memory operation settings (e.g., 193, 195, 197) in response to the sensor data stream (e.g., 121).

At block 269, the computer system (131) having the data storage device (101) predicts, using the artificial neural network (125), a maintenance service of the vehicle (111) based on the sensor data stream (e.g., 121).

Figure 16:
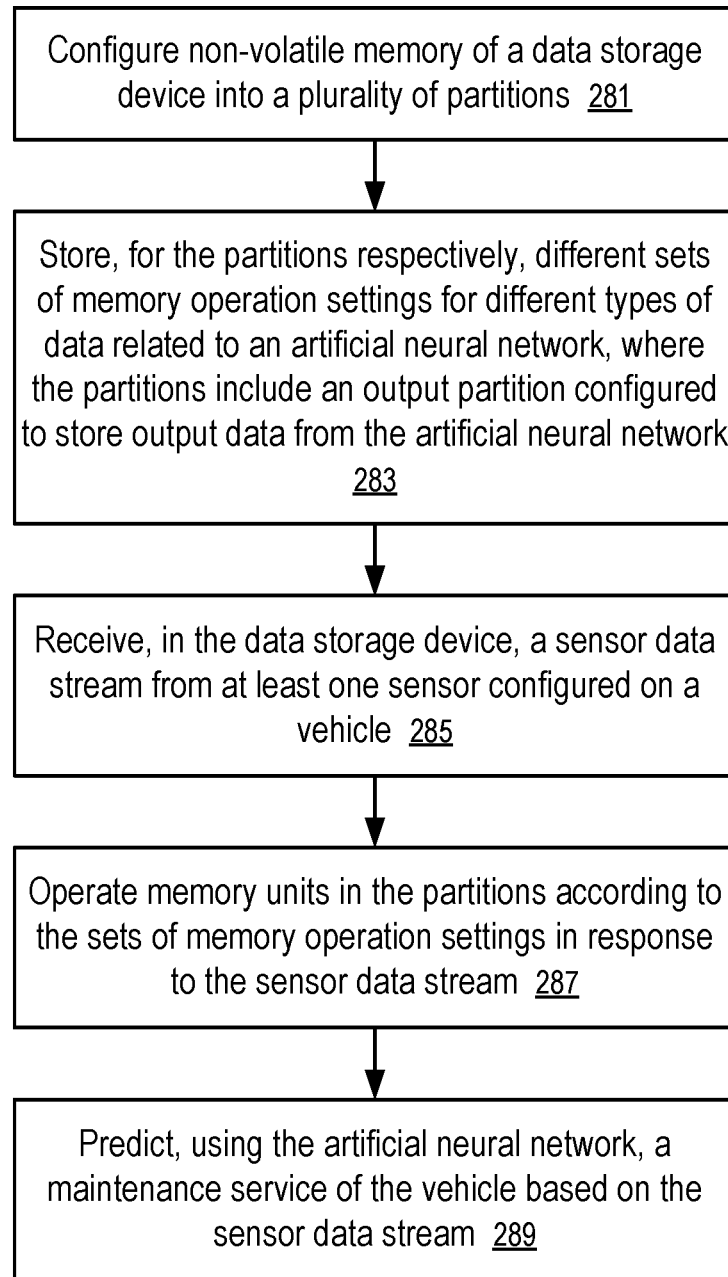

FIG. 16 shows a method of predictive maintenance supported by an input partition according to one embodiment. For example, the method of FIG. 16 can be implemented in a vehicle (111) of FIG. 1 or 2 using a data storage device (101) of FIG. 7 or 10 and/or a storage media component (160) of FIG. 8. For example, the method of FIG. 16 can be used in combination with the method of FIGS. 6, 9, 14, and/or 15.

At block 281, non-volatile memory of a data storage device (101) is configured into a plurality of partitions (e.g., 183, 185, 187, . . . ). The non-volatile memory can have the same type of memory units (e.g., NAND flash memory units) for storing data.

At block 283, the data storage device (101) stores, for the partitions (e.g., 183, 185, 187, . . . ) respectively, different sets of memory operation settings (e.g., 193, 195, 197) for different types of data related to an artificial neural network (125), where the partitions (e.g., 183, 185, 187, . . . ) include an output partition (e.g., 187) configured to store output data for the artificial neural network (125).

For example, the output data stored in the output partition (e.g., 187) can include state data of neurons in the artificial neural network (125). For example, the state data of the neurons in the artificial neural network can identify the activation levels of the neurons for spiking in a spiking neural network. The activation levels can be controlled via a differential equation. Thus, the activation levels can change in response to inputs to the artificial neural network (125) and/or in response to the passage of time.

For example, the output data can include the predictions or classifications generated by the artificial neural network (125) responsive to the sensor data stream.

For example, the memory operation settings configure the output partition to store no more than two bits per memory cell in the non-volatile memory.

At block 285, the data storage device (101) receives a sensor data stream (e.g., 121) from at least one sensor (103) configured on a vehicle (111).

At block 287, a controller (151) of the data storage device (101) operates memory units in the partitions (183, 185, 187, . . . ) according to the sets of memory operation settings (e.g., 193, 195, 197) in response to the sensor data stream (e.g., 121).

At block 289, the computer system (131) having the data storage device (101) predicts, using the artificial neural network (125), a maintenance service of the vehicle (111) based on the sensor data stream (e.g., 121).

For example, the data storage device (101) can include a buffer (152). The buffer (152) can be implemented via volatile memory (e.g., SRAM or DRAM) for access performance faster than the non-volatile memory (e.g., NAND flash memory) of the data storage device (101). The memory operation settings configure the controller (151) to store the output data in the buffer (152) for access by a processor (e.g., 133) via the host interface (157) during or after storing the output data into the output partition (187).

For example, the data storage device (101) can include a neural network accelerator (159) coupled to the controller (151). The neural network accelerator is configured to apply inputs provided to neurons in the artificial neural network (125) to model data of the artificial neural network (125) to generate the output data by one or more output neurons in the artificial neural network (125). In response to the neural network accelerator (159) completing the computation of the output data, the controller is configured to provide the processor (e.g., 133) with an indication of the availability of the output data generated by the artificial neural network (125), such that the processor (e.g., 133) may request the data storage device (101) to transmit the output data.

Optionally, the controller (151) is configured to provide the output data to the processor in parallel with storing the output data into the output partition. For example, the controller (151) can be configured to automatically discard the output data computed for the previously segment of sensor data stream if the processor (e.g., 133) does not request for the transmission of the output data to the processor (e.g., 133) within a predetermined period of time, or before the next version of the output data is available. Optionally, after reporting the availability of the output data to the processor (e.g., 133), the controller (151) can be configured to selectively discard the output data computed for the previously segment of sensor data stream based on a response of the processor (e.g., 133) for the output data to the processor (e.g., 133). For example, the processor (e.g., 133) may request the transmission of the output data to the processor (e.g., 133) without saving the output data into the output partition (e.g., 187) in some situations; and in other situations, the processor (e.g., 133) may request the transmission of the output data to the processor (e.g., 133) and the storing of the output data into the output partition (e.g., 187).

Optionally, output data from the artificial neural network (125) can also be stored into the output partition in a cyclic way (e.g., for the segments of output data for time periods selected by the processor (e.g., 133)).

For example, external inputs to the artificial neural network (125) can be recorded in the input namespace (185) continuously for the last time period of T1. When the sensor data is sampled at a predetermined time interval T2, the input namespace (185) can hold the latest T1/T2 sets of input data. In contrast, external outputs from the artificial neural network (125) can be selectively recorded into the output namespace (187) (e.g., once for every a predetermined period of time T3, where T3 is multiple of T2). The output data can be recorded into the output namespace (187) at a lower frequency; and the output namespace (187) can be allocated to store a predetermined number of sets of output data (e.g., via sequential writes and writes in a cyclic way to keep the last sets of output data).

At least some embodiments disclosed herein include a communication protocol/interface that allows a data storage device to perform neural network acceleration on the fly with reduced data traffic to the host processor (e.g., a central processing unit (CPU)).

For example, the host processor (e.g., 133) of a vehicle (111) can provide write commands to the data storage device (101) to store the model of an artificial neural network in a model partition (e.g., 183). Since the neural network accelerator (159) is configured to apply the model, the data communications sending back the data of the model of ANN (125) to the processor can be reduced or eliminated.

To use the ANN model in classifications and/or predictions, the host processor (e.g., 133) of a vehicle (111) can stream input data for the ANN (125) into the neuron input partition (e.g., 185). The neural network accelerator (159) of the storage device (101) can automatically apply the input data to the model stored in ANN model partition (e.g., 183) in accordance with the address map (191). The data storage device (101) makes the computed outputs available for propagation in the ANN (125). Preferably, the computed outputs are made available to the neural network accelerator (159) through the buffer (152) without the need to store the intermediate outputs into storage media components (e.g., 161 to 163). Thus, the data communications between the host processor (e.g., 133) and the data storage device (101) for the transporting of outputs of neurons can be reduced. When the outputs have propagated to the output neurons in the ANN (125), the data storage device (101) can provide a response to the write request associating with the writing of a set of input data into the neuron input partition (e.g., 185). The response indicates that the external output from neurons in the ANN (125) is available. In response, the host processor (e.g., 133) of a vehicle (111) can optionally issue read commands to retrieve the external outputs for further processing.

Figure 17:
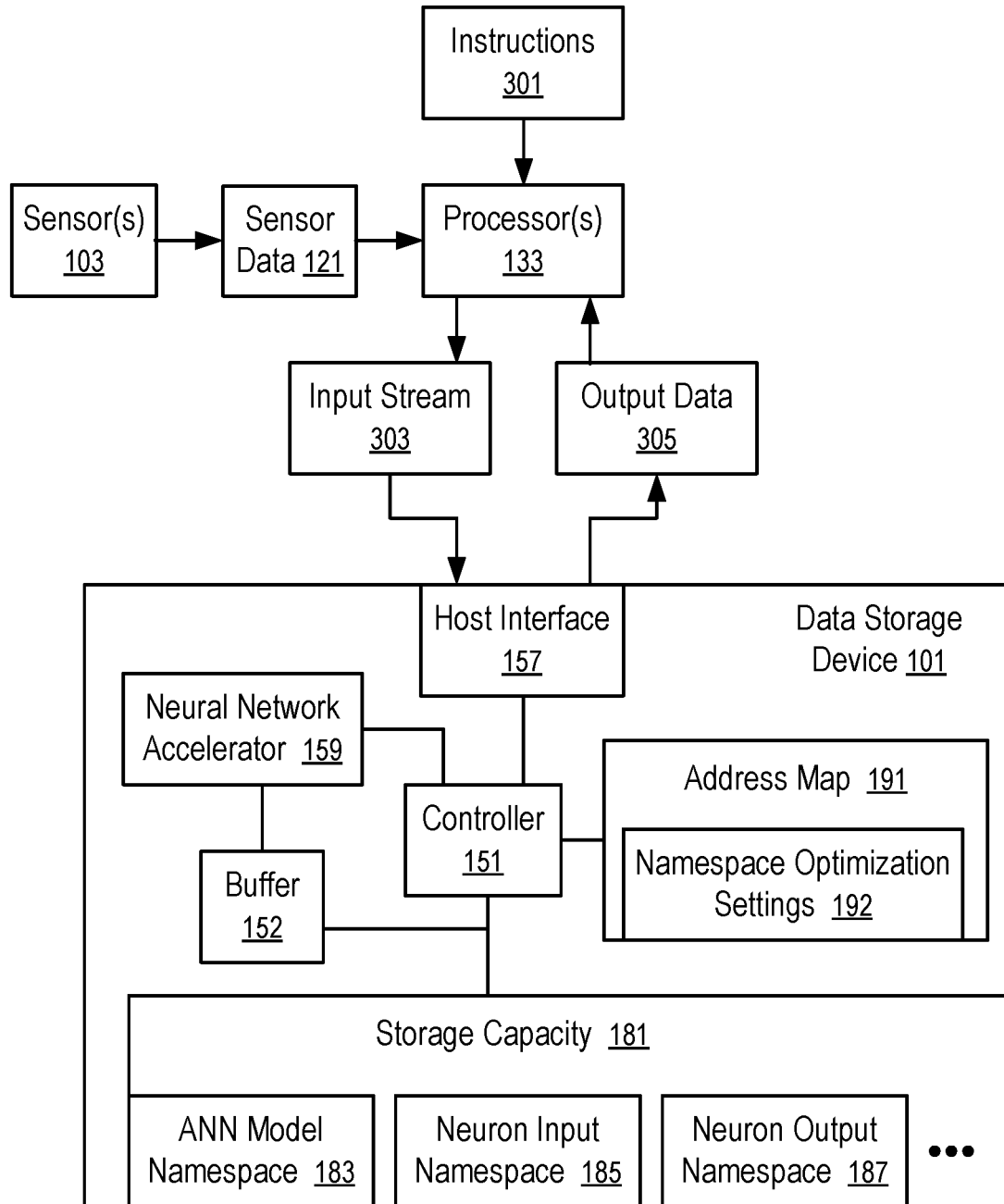
FIG. 17 shows communications with a data storage device to implement neural network computation according to one embodiment.

FIG. 17 shows communications with a data storage device (101) to implement neural network computation according to one embodiment. For example, the communications as illustrated in FIG. 17 can be implemented in the vehicle (111) of FIG. 1 or 2, with a data storage device (101) illustrated in FIG. 7 or 10.

In FIG. 17, the processor(s) (133) can be configured with a simplified set of instructions (301) to perform neural network computation, since some of the computations involving the ANN (125) is performed by the neural network accelerator (159) within the data storage device (101). Thus, it is not necessary to transport the model data back to the processor(s) (133) during the use of the ANN (125) for predictions and/or classifications.

The sensor(s) (103) can generate a continuous stream of sensor data (121) based on a rate for sampling data. The sensor data (121) can be sampled at a fixed, predetermined time interval (e.g., during the operation of the vehicle (111)). The processor(s) (133) can execute the instructions (301) to convert the sensor data (121) into an input stream (303) for input neurons in the ANN (125). Input neurons in the ANN (125) are configured to accept external inputs to the ANN (125); and output neurons are configured to provide external outputs from the ANN (125).

In general, a complete set of input for the ANN (125) at a time instance includes inputs for the entire set of input neurons of the ANN (125). The input stream (303) includes a sequence of input sets for a sequence of time instances that are spaced apart from each other according to the fixed, predetermined time interval.

The data storage device (101) stores the input stream (303) into the neuron input namespace (185) in a cyclic way where the oldest input set corresponding to the oldest time instance of data sampling for data sets currently stored in the neuron input namespace (185) is erased to store the newest set of inputs in the input stream (303).

For each input data set, the neural network accelerator (159) applies the model of the ANN (125) stored in the ANN model namespace (183). The neural network accelerator (159) (or the processor(s) (133)) can control the propagation of signals within the neural network. When the output neurons of the ANN (125) generate their outputs responsive to the input data set, the data storage device (101) can provide to the processor (133) an indication that the neuron output are ready for retrieval. The indication can be configured in a response to the request from the processor(s) (133) to write the input data set into the neuron input namespace (185). The processor(s) (133) can optionally retrieve the output data (305) (e.g., in accordance with conditions and/or criteria programmed in the instructions).

In some embodiments, a trigger parameter is configured in the data storage device (101). When an output parameter in the external output (317) meetings a requirement specified by the trigger parameter, the data storage device provides the response to the request from the processor(s) (133) to write the input data set into the neuron input namespace (185).

Figure 18:
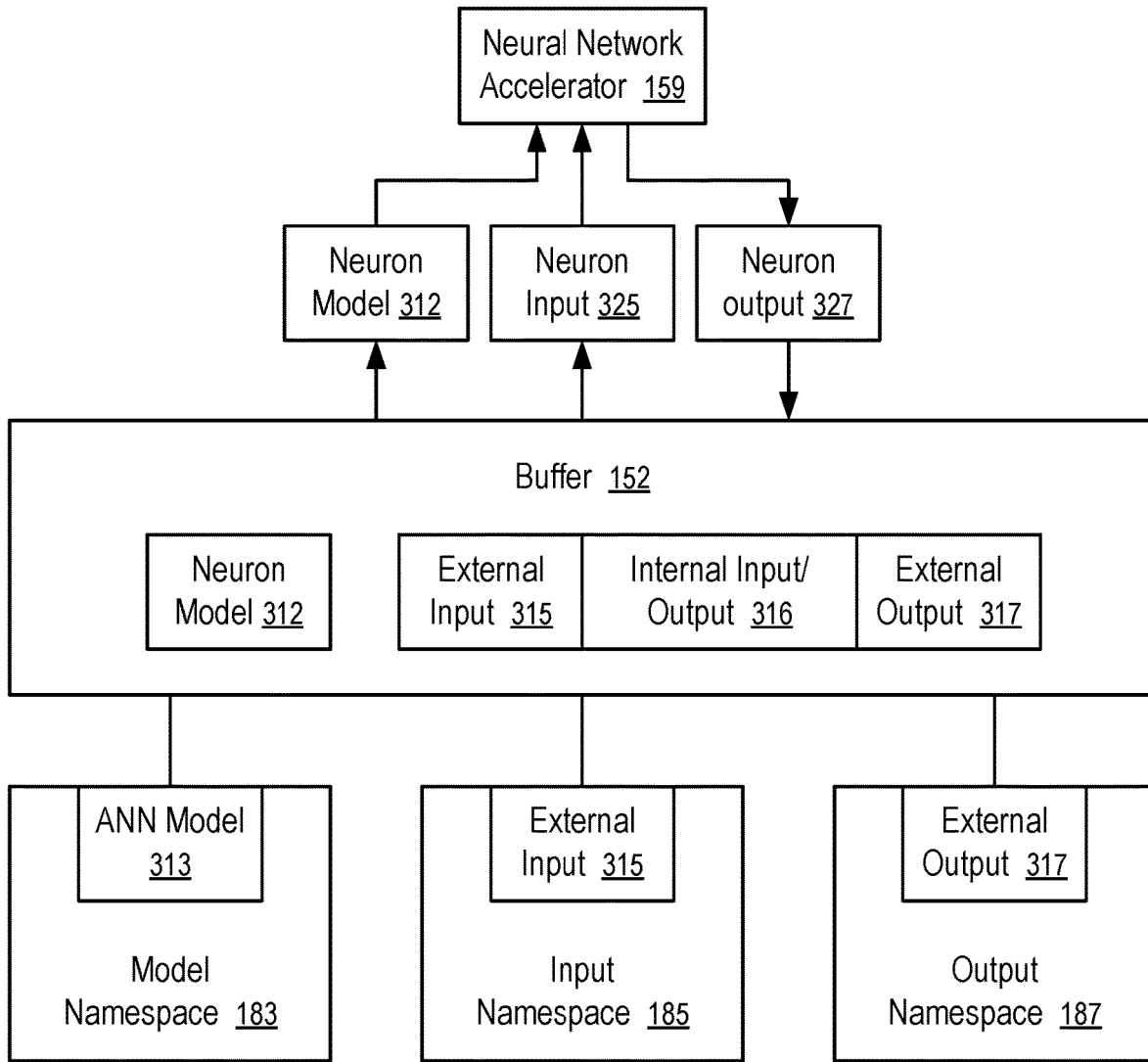
FIG. 18 shows communications within a data storage device to implement neural network computation according to one embodiment.

FIG. 18 shows communications within a data storage device to implement neural network computation according to one embodiment. For example, the communications of FIG. 18 can be implemented a data storage device (101) illustrated in FIG. 7 or 10, in connection with the communications of FIG. 17.

In FIG. 18, the model namespace (183) stores the model (313) of the entire ANN (125). In response to receiving a set of external input (315) for a time instance from the input stream (303) in the buffer (152), the data storage device (101) can write the external input (315) into the input namespace (185) in parallel with retrieving a neuron model (312) containing a portion of the ANN model (313) corresponding to the parameters of the input neurons and/or the identities of neurons connected to the input neurons. The buffer (152) allows the neural network accelerator (159) to combine the neuron model (312) and the external input (325) to generate the output (327) of the input neurons.

In general, the neuron output (327) can include a portion that is the internal output (316) for further propagation within the ANN (125) and/or a portion that is the external output (317) for the processor(s) (133).

The internal output (316) is stored in the buffer (152) as internal input (316) for further propagation in the ANN (125) in a way similar to the generation of neuron outputs (327) from the external input (315). For example, a portion of the internal input (316) can cause the controller (151) and/or the neural network accelerator (159) to retrieve corresponding neuron model (312) relevant to the internal input such that the internal input is applied in the neural network accelerator (159) to the corresponding neuron model (312) to generate their neuron outputs (327).

When the complete set of external output (317) is available in the buffer (152), the external output (317) can be stored in the output namespace (187).

Optionally, the storage device (101) does not store each set of external output (317) corresponding to a set of stored external input (315) sampled at a time instance. For example, the storage device (101) can be configured to store one set of external output (317) for every a predetermined number of sets of external input (e.g., 315). Alternatively, or in combination, the processor(s) (133) can determine whether or not to store the external output (317). For example, the storage device (101) can be configured to store the external output (317) in response to the processor(s) (133) retrieving the external output (317) for further processing. For example, the storage device (101) can be configured to store the external output (317) in response to a write command from the processor(s) (133) after the processing of the external output (317) in the processor(s) (133).

Figure 19:
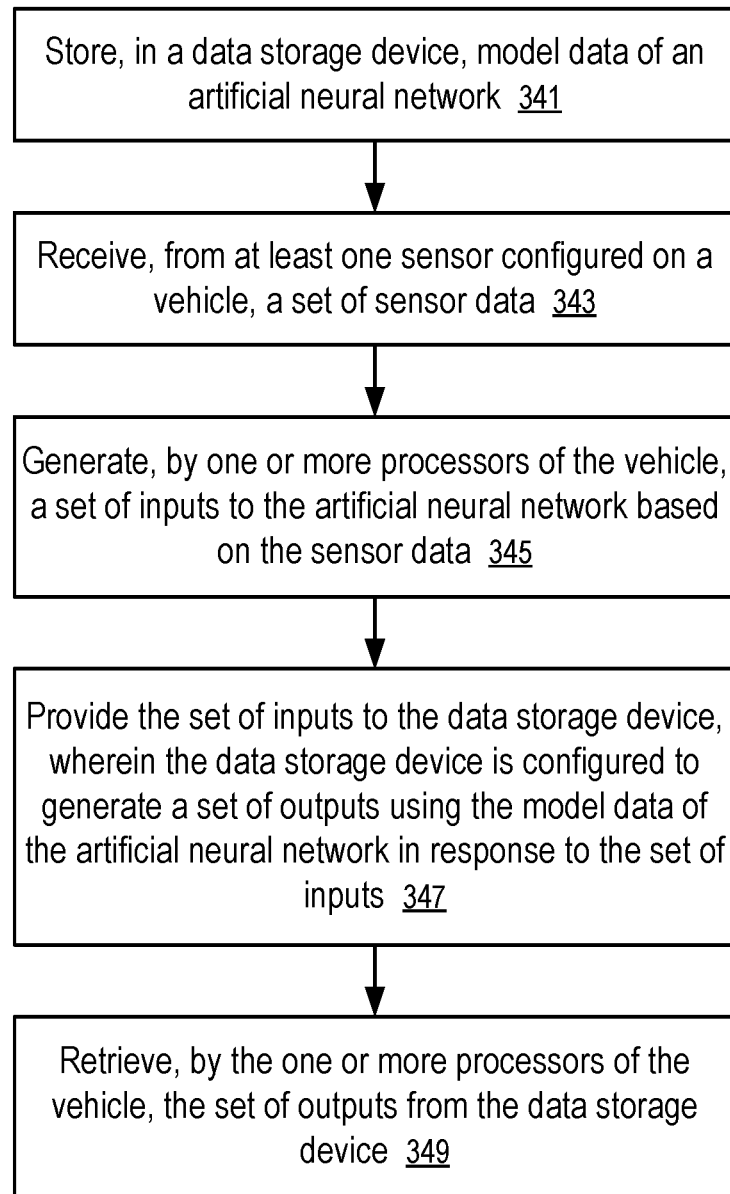
FIG. 19 shows a method of communicating with a data storage device to implement neural network computation according to one embodiment.

FIG. 19 shows a method of communicating with a data storage device to implement neural network computation according to one embodiment. For example, the method of FIG. 19 can be implemented in a vehicle (111) of FIG. 1 or 2 using a data storage device (101) of FIG. 7 or 10 and/or a storage media component (160) of FIG. 8. For example, the method of FIG. 19 can be used in combination with the method of FIGS. 6, 9, 14, 15, and/or 16.

At block 341, one or more processors (133) of a vehicle (111) stores model data (e.g., 313) of an artificial neural network (e.g., 125) into a data storage device (101).

At block 343, the one or more processors (133) of the vehicle (111) receive, from at least one sensor (103) configured on vehicle (111), a set of sensor data.

At block 345, the one or more processors (133) of the vehicle (111) generate a set of inputs to the artificial neural network (e.g., 125) based on the sensor data.

At block 347, the one or more processors (133) of the vehicle (111) provide the set of inputs to the data storage device (101). In response to the set of inputs, the data storage device (101) is configured to generate a set of outputs using the model data (313) of the artificial neural network (e.g., 125).

At block 349, the one or more processors (133) of the vehicle (111) retrieve the set of outputs from the data storage device (101).

For example, the data storage device (101) generates the set of outputs using at least a portion of the model data (183) stored in the data storage device without transmitting the portion of the model data (183) to the one or more processors (133) between the receiving of the set of inputs and the completion of the computation of the set of outputs.

For example, the portion of the model data (183) can include static attributes of neurons in the artificial neural network (e.g., 125) and/or the neuron connectivity data of the artificial neural network (e.g., 125).

For example, to provide of the set of inputs to the data storage device (101), the one or more processors (133) of the vehicle (111) can transmit one or more write commands to the data storage device (101). The one or more write commands are configured to instruct the data storage device (101) to store the set of input in the data storage device (101). After the completion of the computation of the set of outputs in the data storage device (101), the controller (151) of the data storage device (101) can transmit a response to the one or more write commands to the one or more processors (133). The response can include an indication that the set of outputs is available for retrieval by the one or more processors (133).

In response to the indication, the one or more processors (133) can optionally retrieves of the set of outputs from the data storage device (101) by transmitting a read command to the data storage device (101) for the set of outputs (e.g., after a determination to retrieve the set of outputs from the data storage device (101) for processing).

Alternatively, or in combination, the one or more processors (133) of the vehicle (111) can determine whether to store the set of outputs in non-volatile memory of the data storage device. In response to a determination to store the set of outputs in the non-volatile memory of the data storage device (101), one or more processors (133) of the vehicle (111) can transmit a write command to the data storage device (101).

Since the set of outputs is initially generated in the data storage device (101) and then buffered in the buffer (152) (e.g., volatile memory), the data storage device (101) can execute a write command to store the set of outputs into an output namespace (187) without transmitting the set of outputs to the one or more processors (133) and/or receiving the set of outputs from the one or more processors (133) in response to the write commands.

For example, after receiving, from at least one sensor (103) configured on the vehicle (111), a further set of sensor data (121), the one or more processors (133) of the vehicle (111) generate a further set of inputs to the artificial neural network (125) based on the further set of sensor data.

The one or more processors (133) transmits a further command to write the further set of inputs into the data storage device (101); and the data storage device (101) generates a further set of outputs using the model data (183) of the artificial neural network (125) and the further set of inputs. After receiving a response to the further command to write the further set of inputs, the one or more processors (133) can determine to skip the processing of the further set of outputs and transmit, to the data storage device (101), a subsequent write command to store the further set of outputs. In response, the data storage device (101) can write the further set of outputs that is buffered within the data storage device (101) into the output namespace (187), without the transmitting of the further set of outputs from the one or more processors (133) of the vehicle (111) to the data storage device (101) and/or without the transmitting of the further set of outputs from the data storage device (101) to the one or more processors (133) of the vehicle (111).

The neural network techniques discussed above can be used in driver drowsiness detection for vehicle control according to one embodiment.

For example, an artificial neural network can be trained to determine whether a driver of the vehicle is in a drowsy state. A cabin camera can be used to generate still and/or video images of the driver, include the facial images of the driver and/or the posture of the driver. The images are processed in real time by the artificial neural network to classify whether the driver is alert or drowsy. When the artificial neural network classifies the images of the driver as being in a drowsy state, the computer system of the vehicle can be configured to provide gentle instructions to the driver and detect responses from the drive. The reactions to the instructions can be further analyzed to more accurately identify driver drowsiness. In response to driver drowsiness, the vehicle can take further actions, such as activating an advanced driver assistance system (ADAS) to take emergence measures. For example, the ADAS can slow down and/or stop the vehicle, and/or enable autonomous driving mode to avoid potential accidents that may result from driver drowsiness.

Figure 20:
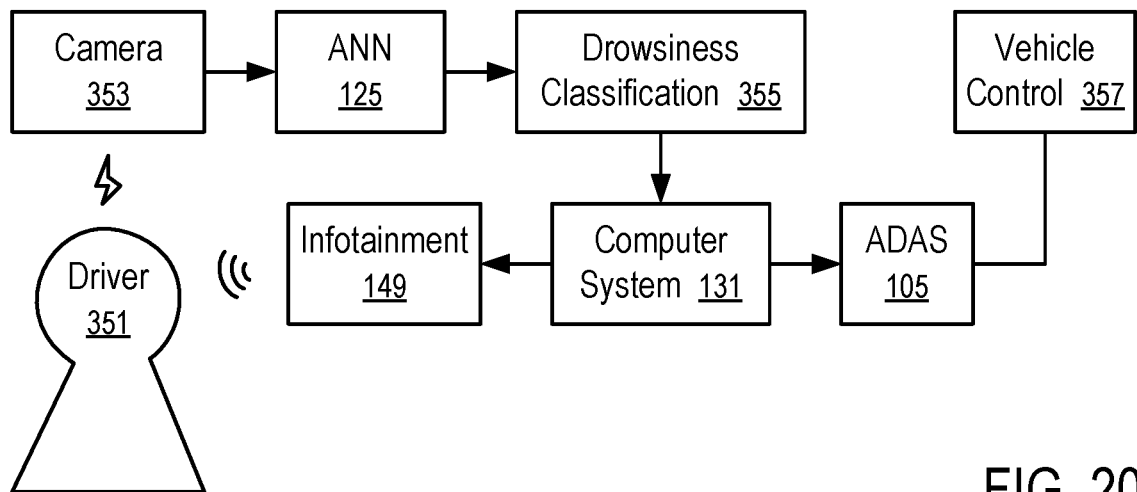
FIG. 20 shows a system to control a vehicle based on drowsiness detection according to one embodiment.

FIG. 20 shows a system to control a vehicle based on drowsiness detection according to one embodiment. For example, the system of FIG. 20 can be implemented with a data storage device (101) of FIG. 7 or 10 in a vehicle (111) illustrated in FIG. 1 or 2.

In FIG. 20, the system includes a camera (353) configured to monitor the driver (351) of the vehicle (111).

For example, the camera (353) can be configured on a rear view mirror of the vehicle (111), on a side view mirror of the vehicle (111), on the instrument panel of the vehicle (111), or on the display panel of infotainment system (149) of the vehicle (111), etc. The camera (353) is configured to face the driver (351) to capture images showing the facial image of the driver (351) and/or the posture of the driver (351). The posture of the driver (351) can include the position and/or orientation of the head of the driver (351) relative to the torso of the driver (351) and/or the steering wheel of the vehicle (111).

The camera (343) can capture a sequence of images of the driver (351) for analysis in an artificial neural network (125). The images can be still images captured at a predetermined time interval, or video images in a video stream. Each of the images can be analyzed to extract features relevant to drowsiness classification (355). For example, the eyes of the driver (351) in the image can be identified to measure the opening of eyelids. For example, key features on a face can be identified from the facial image of the driver (351) to determine facial expression of the driver (351). For example, the orientation of the head of the driver (351) relative to the vehicle (111) and/or the torso of the driver (351) can be measured from the image.

The ANN (125) is configured to analyze the time sequence of changes in features extracted from the images captured by the camera (353). A temporal analysis of the feature changes can capture the patterns indicative of drowsiness.

Initially, the ANN (125) can be trained using images captured from persons during time periods in which they are known to be drowsy and during other time periods in which they are known to be alert.

Subsequently and/or alternatively, the ANN (125) can be trained using images of the driver (351) during time periods in which the driver (351) is predetermined to be not drowsy (e.g., in the morning and/or during the beginning of a trip). The training can customize the ANN (125) for the driver (351) to recognize the patterns associated with alert states of the driver (351) such that when a current state deviates from recognized alert states, a drowsiness classification (355) can be made.

When the ANN (125) a drowsiness classification (355) indicating that the driver (351) is in a drowsy state, the drowsiness classification (355) causes the computer system (131) of the vehicle (111) to interact with the driver (351) via the infotainment system (149). For example, the computer system (131) may instruct the drive to take a brief look at the rear view mirror or a side view mirror, or glance the front left side or the front right side of the vehicle, or provide a gesture such as nodding or shaking head, raising a hand, etc. The instruction can be provided via voice at varying volumes to test awareness of the driver. The response to the instructions can be detected via the camera (353). From the tests, the computer system (131) can confirm the previously classification of drowsiness or reject the previously classification as false alarm.

Optionally, the data storage device (101) automatically stores a copy of the input data to the ANN (125) that leads to a classification (355) of drowsiness. When the classification (355) is subsequently confirmed or rejected, the stored input data can be used to further train the ANN (125) to improve the accuracy of the ANN (125).

Optionally, the camera (353) and the data storage device (101) having the ANN (125) can be configured as a drowsiness detection module. The module communicates its drowsiness classifications (355) to the computer system (131) via a wired or wireless connection. Alternatively, a portion of the data storage device (101) of the computer system (131) of the vehicle (111) is used to process the input from the camera (353) that is configured to face the driver (351).

When the computer system (131) determines that the driver (351) is in a drowsy state, the computer system (131) can optionally transfer the control from the driver (351) to an advanced driver assistance system (ADAS) (105) of the vehicle (111). For example, when the ADAS (105) has a full autonomous driving capability, the ADAS (105) can operate the vehicle control (357). Control signals from the driver (351) may be validated against the decisions from the ADAS (105) and/or optionally discarded. For example, the ADAS (105) may activate the emergency light of the vehicle (111) and slow down the vehicle (111) gradually and/or limit the speed of the vehicle (111) when the computer system (131) determines that the driver (351) is in a drowsy state.

Figure 21:
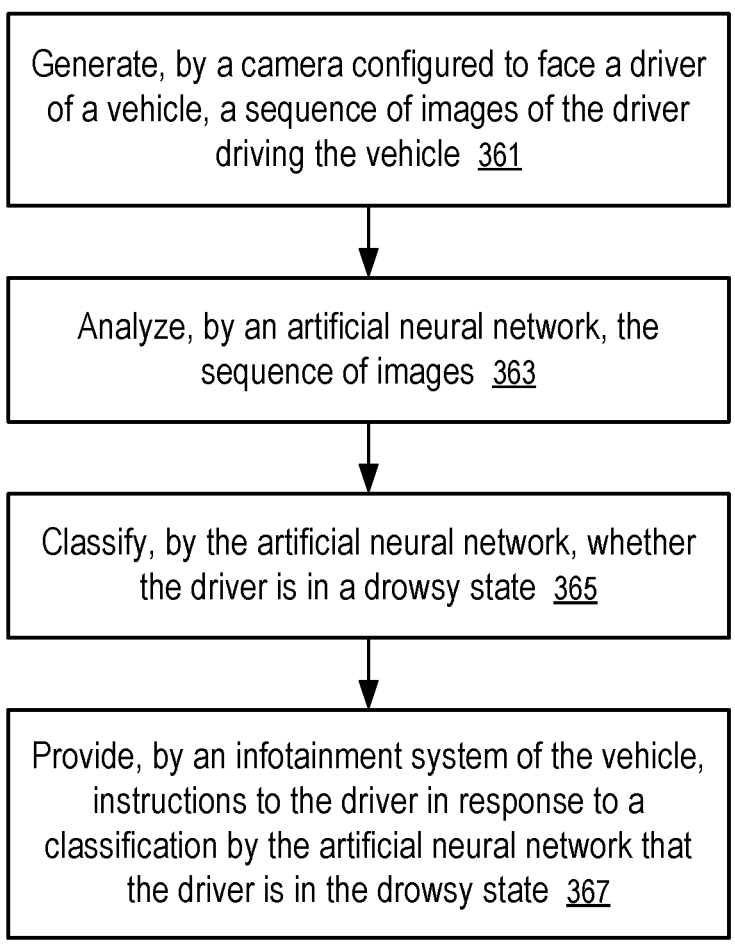
FIG. 21 shows a method of drowsiness detection for vehicle control according to one embodiment.

FIG. 21 shows a method of drowsiness detection for vehicle control according to one embodiment. For example, the method of FIG. 21 can be implemented in a vehicle (111) of FIG. 1 or 2 using a data storage device (101) of FIG. 7 or 10 and/or a storage media component (160) of FIG. 8. For example, the method of FIG. 21 can be used in combination with the method of FIGS. 6, 9, 14, 15, 16, and/or 19.

At block 361, a camera (353), configured to face a driver (351) of a vehicle (111), generates a sequence of images of the driver (351) driving the vehicle (111).

At block 363, an artificial neural network (125) analyzes the sequence of images generated by the camera (353).

At block 365, the artificial neural network (125) classifies whether the driver (351) is in a drowsy state.

At block 367, in response to a classification (355) by the artificial neural network (125) that the driver (351) is in the drowsy state, an infotainment system (149) of the vehicle (111) provides instructions to the driver (351).

For example, the infotainment system (149) can be configured to provide the instructions via voice. The voice instructions can be provided at varying volume levels to test alertness/awareness of the driver (351).

For example, the instructions can be configured to request the driver (351) to provide a response detectable in subsequent images captured by the camera (353). For example, the requested response can be a gesture by the driver (351). The driver (351) can make the gesture by moving the viewing direction of the eyes of the driver (351), by moving the head of the driver (351), by moving a hand of the driver (351), and/or by moving one or more fingers of the driver (351). In some implementations, the gesture can be customized for the driver (351); and the driver (351) can pre-define the gesture used to indicate alertness by making the move and train the artificial neural network (125) to recognize the gesture.

The artificial neural network (125) can be further configured to analyze the subsequent images captured by the camera (353) to confirm, based on lack of the response requested via the instructions, the classification of drowsiness.

Optionally, the driver (351) can provide a response via voice to indicate non-drowsiness. A microphone can be configured to receive the voice response; and the artificial neural network (125) can be further configured to analyze the inputs from the microphone to detect the voice response or the absence of the voice response.

Optionally, the vehicle (111) can include an advanced driver assistance system (ADAS) (105). For example, in response to a confirmation of the drowsiness classification (355), the ADAS (105) can at least partially control the vehicle (111), such as activating an autonomous drive function to fully control the driving of the vehicle (111), limiting a speed of the vehicle (111), slowing down and stopping the vehicle (111), placing the vehicle (111) in a safe state and/or location, and/or validating control signals provided by the driver (351).

Optionally, the artificial neural network (125) can be trained to recognize patterns in training images generated by the camera (353), where the patterns are associated with the driver being in an alert state and the training images are generated during a time period in which the driver is predetermined to be in the alert state.

For example, the artificial neural network (125) can include a spiking neural network configured for temporal analysis of features extracted from the images from the camera (353).

Optionally, the camera (353) and the data storage device (101) can be configured as a drowsiness detection module. The data storage device (101) stores model data (e.g., 313) of the artificial neural network (125). In response to receiving the sequence of images in the data storage device (101), the data storage device (101) uses its neural network accelerator (159) and the model data (e.g., 313) to analyze the sequence of images and classify whether the driver is in a drowsy state. In response to a drowsiness classification (355), the drowsiness detection module communicates the classification (355) to a computer system (131) of the vehicle (111), which causes an infotainment system (149) of the vehicle (111) to provide the instructions to the driver (351) to test alertness of the driver (351).

The server (119), the computer system (131), and/or the data storage device (101) can each be implemented as one or more data processing systems.

The present disclosure includes methods and apparatuses which perform the methods described above, including data processing systems which perform these methods, and computer readable media containing instructions which when executed on data processing systems cause the systems to perform these methods.

A typical data processing system may include includes an inter-connect (e.g., bus and system core logic), which interconnects a microprocessor(s) and memory. The microprocessor is typically coupled to cache memory.

The inter-connect interconnects the microprocessor(s) and the memory together and also interconnects them to input/output (I/O) device(s) via I/O controller(s). I/O devices may include a display device and/or peripheral devices, such as mice, keyboards, modems, network interfaces, printers, scanners, video cameras and other devices known in the art. In one embodiment, when the data processing system is a server system, some of the I/O devices, such as printers, scanners, mice, and/or keyboards, are optional.

The inter-connect can include one or more buses connected to one another through various bridges, controllers and/or adapters. In one embodiment the I/O controllers include a USB (Universal Serial Bus) adapter for controlling USB peripherals, and/or an IEEE-1394 bus adapter for controlling IEEE-1394 peripherals.

The memory may include one or more of: ROM (Read Only Memory), volatile RAM (Random Access Memory), and non-volatile memory, such as hard drive, flash memory, etc.

Volatile RAM is typically implemented as dynamic RAM (DRAM) which requires power continually in order to refresh or maintain the data in the memory. Non-volatile memory is typically a magnetic hard drive, a magnetic optical drive, an optical drive (e.g., a DVD RAM), or other type of memory system which maintains data even after power is removed from the system. The non-volatile memory may also be a random access memory.

The non-volatile memory can be a local device coupled directly to the rest of the components in the data processing system. A non-volatile memory that is remote from the system, such as a network storage device coupled to the data processing system through a network interface such as a modem or Ethernet interface, can also be used.

In the present disclosure, some functions and operations are described as being performed by or caused by software code to simplify description. However, such expressions are also used to specify that the functions result from execution of the code/instructions by a processor, such as a microprocessor.

Alternatively, or in combination, the functions and operations as described here can be implemented using special purpose circuitry, with or without software instructions, such as using Application-Specific Integrated Circuit (ASIC) or Field-Programmable Gate Array (FPGA). Embodiments can be implemented using hardwired circuitry without software instructions, or in combination with software instructions. Thus, the techniques are limited neither to any specific combination of hardware circuitry and software, nor to any particular source for the instructions executed by the data processing system.

While one embodiment can be implemented in fully functioning computers and computer systems, various embodiments are capable of being distributed as a computing product in a variety of forms and are capable of being applied regardless of the particular type of machine or computer-readable media used to actually effect the distribution.

At least some aspects disclosed can be embodied, at least in part, in software. That is, the techniques may be carried out in a computer system or other data processing system in response to its processor, such as a microprocessor, executing sequences of instructions contained in a memory, such as ROM, volatile RAM, non-volatile memory, cache or a remote storage device.

Routines executed to implement the embodiments may be implemented as part of an operating system or a specific application, component, program, object, module or sequence of instructions referred to as "computer programs." The computer programs typically include one or more instructions set at various times in various memory and storage devices in a computer, and that, when read and executed by one or more processors in a computer, cause the computer to perform operations necessary to execute elements involving the various aspects.

A machine readable medium can be used to store software and data which when executed by a data processing system causes the system to perform various methods. The executable software and data may be stored in various places including for example ROM, volatile RAM, non-volatile memory and/or cache. Portions of this software and/or data may be stored in any one of these storage devices. Further, the data and instructions can be obtained from centralized servers or peer to peer networks. Different portions of the data and instructions can be obtained from different centralized servers and/or peer to peer networks at different times and in different communication sessions or in a same communication session. The data and instructions can be obtained in entirety prior to the execution of the applications. Alternatively, portions of the data and instructions can be obtained dynamically, just in time, when needed for execution. Thus, it is not required that the data and instructions be on a machine readable medium in entirety at a particular instance of time.

Examples of computer-readable media include but are not limited to non-transitory, recordable and non-recordable type media such as volatile and non-volatile memory devices, read only memory (ROM), random access memory (RAM), flash memory devices, floppy and other removable disks, magnetic disk storage media, optical storage media (e.g., Compact Disk Read-Only Memory (CD ROM), Digital Versatile Disks (DVDs), etc.), among others. The computer-readable media may store the instructions.

The instructions may also be embodied in digital and analog communication links for electrical, optical, acoustical or other forms of propagated signals, such as carrier waves, infrared signals, digital signals, etc. However, propagated signals, such as carrier waves, infrared signals, digital signals, etc. are not tangible machine readable medium and are not configured to store instructions.

In general, a machine readable medium includes any mechanism that provides (i.e., stores and/or transmits) information in a form accessible by a machine (e.g., a computer, network device, personal digital assistant, manufacturing tool, any device with a set of one or more processors, etc.).

In various embodiments, hardwired circuitry may be used in combination with software instructions to implement the techniques. Thus, the techniques are neither limited to any specific combination of hardware circuitry and software nor to any particular source for the instructions executed by the data processing system.

The above description and drawings are illustrative and are not to be construed as limiting. Numerous specific details are described to provide a thorough understanding. However, in certain instances, well known or conventional details are not described in order to avoid obscuring the description. References to one or an embodiment in the present disclosure are not necessarily references to the same embodiment; and, such references mean at least one.

In the foregoing specification, the disclosure has been described with reference to specific exemplary embodiments thereof. It will be evident that various modifications may be made thereto without departing from the broader spirit and scope as set forth in the following claims. The specification and drawings are, accordingly, to be regarded in an illustrative sense rather than a restrictive sense.

What is claimed is:

1. A vehicle, comprising:
   a camera configured to face a driver of the vehicle and generate a sequence of images of the driver driving the vehicle;
   an artificial neural network configured to analyze the sequence of images and classify, based on the sequence of images, whether the driver is in a drowsy state; and
   an infotainment system configured to provide instructions to the driver in response to a classification by the artificial neural network that the driver is in the drowsy state;
   wherein the infotainment system is configured to provide the instructions via voice at varying volume levels to test alertness of the driver.

2. The vehicle of claim 1, wherein the instructions are configured to request the driver to provide a response detectable in subsequent images captured by the camera.

3. The vehicle of claim 2, wherein the response includes a gesture by the driver.

4. The vehicle of claim 2, wherein the artificial neural network is further configured to analyze the subsequent images captured by the camera to confirm, based on lack of the response requested via the instructions, the classification of drowsiness.

5. The vehicle of claim 4, further comprising:
   an advanced driver assistance system configured to at least partially control the vehicle in response to a confirmation of the classification.

6. The vehicle of claim 5, wherein the advanced driver assistance system has an autonomous drive function that is activated in response to the confirmation of the classification.

7. The vehicle of claim 5, wherein the advanced driver assistance system is configured to place the vehicle in a safe state in response to the confirmation of the classification.

8. The vehicle of claim 5, wherein the advanced driver assistance system is configured to slow down and stop the vehicle in response to the confirmation of the classification.

9. The vehicle of claim 5, wherein the advanced driver assistance system is configured to limit a speed of the vehicle in response to the confirmation of the classification.

10. The vehicle of claim 5, wherein the advanced driver assistance system is configured to validate control signals provided by the driver in response to the confirmation of the classification.

11. A method, comprising:
generating, by a camera configured to face a driver of a vehicle, a sequence of images of the driver driving the vehicle;
analyzing, by an artificial neural network, the sequence of images as a function of time;
classifying, by the artificial neural network, whether the driver is in a drowsy state;
providing, by an infotainment system of the vehicle, instructions to the driver in response to a classification by the artificial neural network that the driver is in the drowsy state; and
providing instructions to the driver to request for a response detectable via the camera, in response to the classification of drowsiness.

12. The method of claim 11, further comprising:
training, in the vehicle, the artificial neural network to recognize patterns in training images generated by the camera, wherein the patterns are associated with the driver being in an alert state and the training images are generated during a time period in which the driver is predetermined to be in the alert state.

13. The method of claim 12, wherein the artificial neural network includes a spiking neural network.

14. The method of claim 11, further comprising:
generating subsequent images by the camera following the instructions; and
determining a confirmation of the classification of drowsiness based on an analysis of the subsequent images.

15. The method of claim 11, wherein the analysis of the subsequent images is performed by the artificial neural network.

16. An apparatus, comprising:
a camera configured to face a driver of a vehicle and generate a sequence of images of the driver driving the vehicle; and
a data storage device configured to store model data of an artificial neural network, wherein in response to receiving the sequence of images in the data storage device, the data storage device is configured to analyze the sequence of images and classify whether the driver is in a drowsy state based on the sequence of images;
wherein the apparatus is configured to communicate, to a computer system of the vehicle, a classification by the artificial neural network that the driver is in the drowsy state, to cause an infotainment system of the vehicle to provide instructions to the driver to test alertness of the driver.

17. The apparatus of claim 16, wherein the instructions are configured to request the driver to provide a response detectable via the camera; and the camera is further configured to generate subsequent images following the instructions and the data storage device is further configured to determine a confirmation of the classification of drowsiness based on an analysis of the subsequent images in the artificial neural network.

* * * * *